(12) United States Patent
Platten et al.

(10) Patent No.: US 9,593,062 B2
(45) Date of Patent: Mar. 14, 2017

(54) MEANS AND METHODS FOR TREATING AND/OR PREVENTING NATURAL AHR LIGAND-DEPENDENT CANCER

(75) Inventors: Michael Platten, Dossenheim (DE); Christiane Opitz, Weinheim (DE); Wolfgang Wick, Heidelberg (DE); Ulrike Litzenburger, Dossenheim (DE)

(73) Assignee: DEUTSCHLAND KREBSFORSCHUNGSZENTRUM, Heidelberg (DE)

( * ) Notice: Subject to any disclaimer, the term of this patent is extended or adjusted under 35 U.S.C. 154(b) by 29 days.

(21) Appl. No.: 14/343,350

(22) PCT Filed: Sep. 7, 2012

(86) PCT No.: PCT/EP2012/067504
§ 371 (c)(1),
(2), (4) Date: May 30, 2014

(87) PCT Pub. No.: WO2013/034685
PCT Pub. Date: Mar. 14, 2013

(65) Prior Publication Data
US 2014/0294860 A1 Oct. 2, 2014

Related U.S. Application Data

(60) Provisional application No. 61/531,861, filed on Sep. 7, 2011.

(51) Int. Cl.
| | | |
|---|---|---|
| *A61K 31/352* | (2006.01) |
| *A61K 31/35* | (2006.01) |
| *C07C 49/755* | (2006.01) |
| *A61K 31/415* | (2006.01) |
| *C12N 15/113* | (2010.01) |
| *A61K 31/655* | (2006.01) |
| *A61K 38/00* | (2006.01) |
| *C07K 16/28* | (2006.01) |
| *C12N 15/11* | (2006.01) |

(52) U.S. Cl.
CPC .......... *C07C 49/755* (2013.01); *A61K 31/352* (2013.01); *A61K 31/415* (2013.01); *A61K 31/655* (2013.01); *A61K 38/00* (2013.01); *C07K 16/28* (2013.01); *C12N 15/11* (2013.01); *C12N 15/1137* (2013.01); *C12N 15/1138* (2013.01); *C12N 2310/14* (2013.01); *C12Y 113/11011* (2013.01); *C12Y 113/11017* (2013.01)

(58) Field of Classification Search
CPC ............................ A61K 31/35; A61K 31/352
USPC ................................................ 514/456, 681
See application file for complete search history.

(56) References Cited

U.S. PATENT DOCUMENTS

2008/0287374 A1* 11/2008 Yamazaki ............ A61K 31/121
514/25
2010/0183564 A1 7/2010 Boitano et al.

FOREIGN PATENT DOCUMENTS

| JP | 2004-123728 | 4/2004 |
|---|---|---|
| WO | WO 99/32619 | 7/1999 |
| WO | WO 01/29058 A1 | 4/2001 |
| WO | WO 2007/128723 A1 | 11/2007 |
| WO | WO 2010/008427 A1 | 1/2010 |

OTHER PUBLICATIONS

Zhang et al. (Environ. Health Perspec., 2003, 111: 1877-1882).*
Byers, T. (CA Cancer Journal, 1999, 49: 353-361).*
Shen et al. (Neuroscience, 2006, 140: 477-489).*
Abel et al., "An Introduction to the Molecular Basics of Aryl Hydrocarbon Receptor Biology," *Biol. Chem.*, vol. 391, pp. 1235-1248 (2010).
Ball et al., "Characterization of an indoleamine 2,3-dioxygenase-like protein found in humans and mice," *Gene*, vol. 396, No. 1, pp. 203-213 (2007).
Bartel, "MicroRNAs: Target recognition and Regulatory Functions," *Cell*, vol. 136, No. 2, pp. 215-233 (2009).
Bothe et al., "Epigallocatechin-3-gallate does not affect the activity of enzymes involved in metabolic activation and cellular excretion of benzo[a]pyrene in human colon carcinoma cells," *Toxicology Letters*, vol. 203, No. 3, pp. 258-264 (2011).
Cao et al., "DNA constructs designed to produce short hairpin, interfering RNAs in transgenic mice sometimes show early lethality and an interferon response," *J. Appl. Genet.*, vol. 46, No. 2, pp. 217-225 (2005).
DiPucchio et al., "Inhibitors of Indoleamine 2,3-dioxygenase: a review of novel patented lead compounds," *Expert Opin. Ther. Pat.*, vol. 20, pp. 229-250 (2010).
Ellington et al., "In Vitro Selection of RNA Molecules that Bind Specific Ligands," *Nature*, vol. 346, pp. 818-822 (1990).
Fire et al., "Patent and specific genetic interference by double-stranded RNA in Caenorhabditis elegans," *Nature*, vol. 391, pp. 806-811 (1998).
Fire et al., "RNA-triggered gene silencing," *Trends Genet.*, vol. 15, pp. 358-363 (1999).

(Continued)

*Primary Examiner* — Yan Xiao
(74) *Attorney, Agent, or Firm* — Foley & Lardner LLP

(57) ABSTRACT

The present invention relates to the field of cancer therapeutics and treatment of cancer. In particular, it relates to a method for treating and/or preventing a natural AHR ligand-dependent cancer comprising administering to a subject suffering from said cancer a therapeutically effective amount of an AHR inhibitor. Moreover, contemplated is a AHR inhibitor for use in treating and/or preventing a natural AHR ligand-dependent cancer.

2 Claims, 24 Drawing Sheets

(56) References Cited

OTHER PUBLICATIONS

Figure 1:
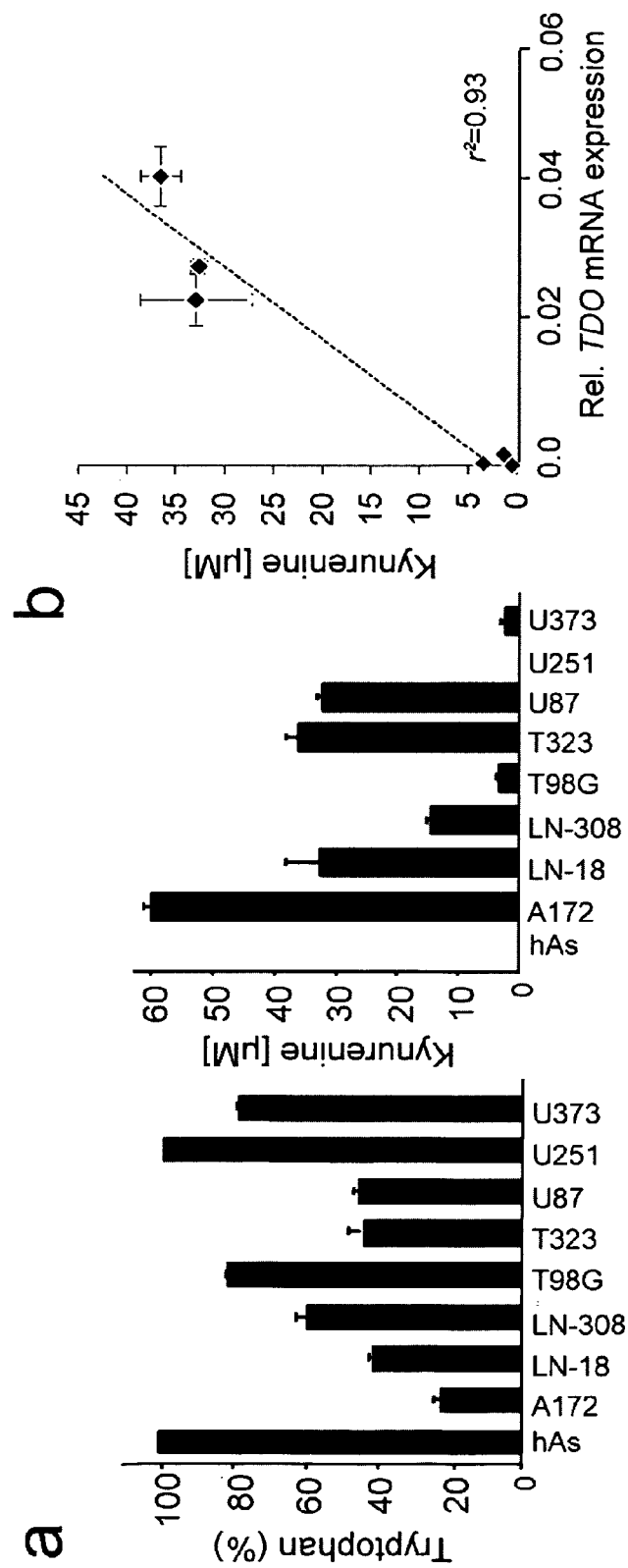
Figure 1:
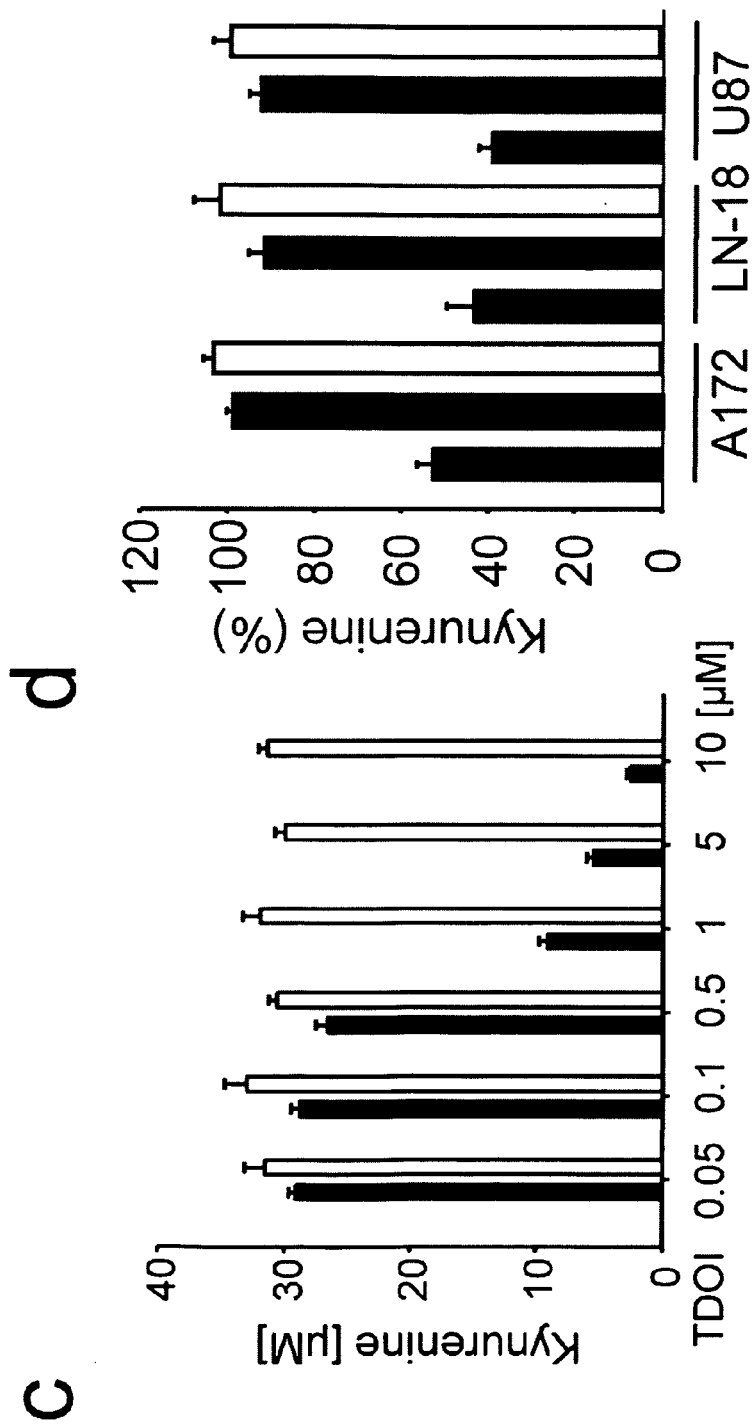
Figure 1:
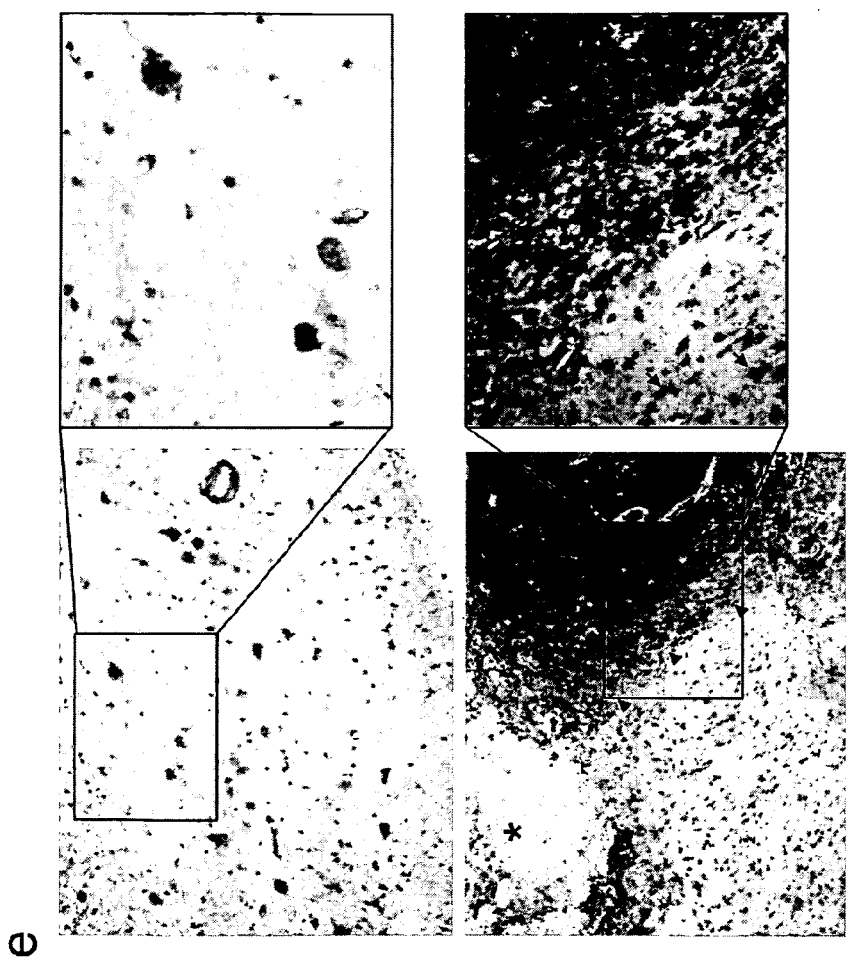
Figure 1:
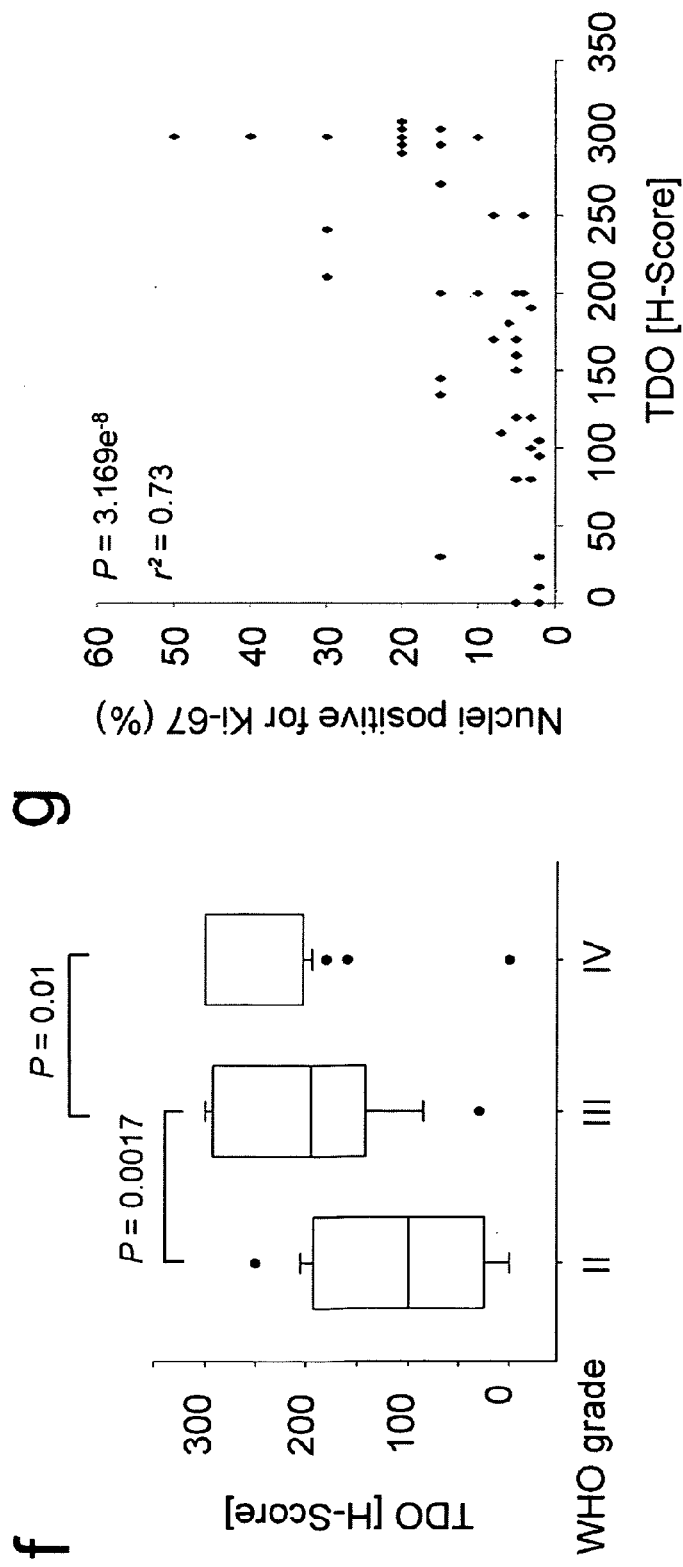
Figure 1:
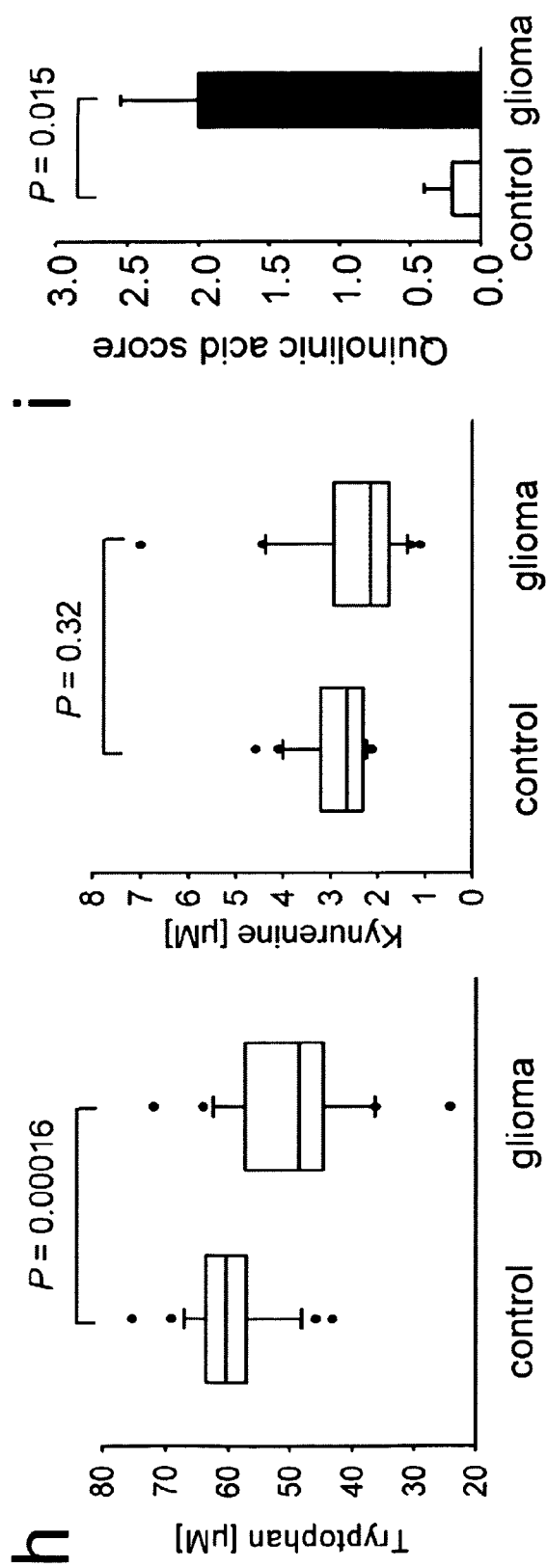

Galfre et al., "Preparation of Monoclonal Antibodies: Strategies and Procedures," *Methods in Enzymology*, vol. 73, pp. 3-46 (1981).
Gardlik et al., "Vectors and delivery systems in gene therapy," *Med. Sci. Monit.*, vol. 11, No. 4, pp. RA110-RA121 (2005).
Gramatzki et al., "Aryl Hydrocarbon Receptor Inhibition Downregulates the TGF-β/Smad Pathway in Human Glioblastoma Cells," *Oncogene*, vol. 28, pp. 2593-2605 (2009).
Kalota et al., "Progress in the Development of Nucleic Acid Therapeutics for Cancer," *Cancer Biology & Therapy*, vol. 3, No. 1, pp. 4-12 (2004).
Khan, Ribozyme: A clinical tool, *Clinica Chimica Acta*, vol. 367, pp. 20-27 (2006).
Kohler et al., "Continuous Cultures of Fused Cells Secreting Antibody of Predefined Specificity," *Nature*, vol. 256, pp. 495-497 (1975).
Lee et al., "3'4'-Dimethoxyflavone as an Aryl Hydrocarbon Receptor Antagonist in Human Breast Cancer Cells," *Toxicological Sciences*, vol. 58, pp. 235-242 (2000).
Li et al., "Therapeutic MicroRNA Strategies in Human Cancer," *The AAPS Journ.*, vol. 11, No. 4, pp. 747-757 (2009).
Löb et al., Inhibitors of Indoleamine-2, 3-Dioxygenase for Cancer Therapy: Can we see the wood for treas?, *Nat Rev Cancer*, vol. 9, No. 6, pp. 445-452 (2009).
McIntyre et al., "Design and cloning strategies for constructing shRNA expression vectors," vol. 6, pp. 1-8 (2006).
Meir et al., "Activation of the transcription factor aryl hydrocarbon receptor increases IL17 and inhibits IL6 suppressing the growth of hepatocellular carcinoma: a novel method for nuclear receptor depenent-tregs directed anti-tumor therapy," *Hepatology*, vol. 50, No. 4, Suppl. S, pp. 1148A (2009).
Metz et al., "Novel Tryptophan Catabolic Enzyme IDO2 Is the Preferred Biochemical Target of the Antitumor Indoleamine 2,3-Dioxygenase Inhibitory Compound D-1-Methyl-Tryptophan," *Cancer Res*. vol. 67, No. 15, pp. 7082-7087 (2007).
Mezrich et al., "An Interaction between Kynurenine and the Aryl Hydrocarbon Receptor Can Generate Regulatory T Cells," *J. Immunol.*, vol. 185, pp. 3190-3198 (2010).
Miller et al., "Expression of the kynurenine pathway enzyme tryptophan 2,3-dioxygenase is increased in the frontal cortex of individuals with schizophrenia," *Neurobiol. Disease*, vol. 15, No. 3, pp. 618-629 (2004).
Miller et al., "Benzo-[α]-pyrene increases invasion in MDA-MB-231 breast cancer cells via increased COX-II expression and prostaglandin $E_2$ ($PGE_2$) output," *Clin. & Experimental Metastasis*, vol. 22, pp. 149-156 (2005).
Mohammadi-Bardbori, et al., "Quercetin, Resveratrol, and Curcumin Are Indirect Activators of the Aryl Hydrocarbon Receptor (AHR)," *Chem. Research in Toxicology*, vol. 25, No. 9, pp. 1878-1884 (2012).
Morcos, "Achieving Targeted and Quantifiable Alteration of mRNA splicing with Morpholino Oligos," *Biochem Biophys. Res. Commun.*, vol. 358, No. 2, pp. 521-527 (2007).
Muller et al., "Inhibition of indoleamine 2,3-dioxygenase, an immunoregulatory target of the cancer suppression gene Bin1, potentiates cancer chemotherapy," *Nat Med*, vol. 11, No. 3, pp. 312-319 (2005).
Munn et al., Indoleamine 2, 3-dioxygenase and Tumor-Induced Tolerance, *J. Clin. Invest.*, No. 117, pp. 1147-1154 (2007).
Nair et al., UVR Exposure Sensitizes Keratinocytes to DNA Adduct Formulation, *Cancer Prevention Research*, vol. 2, No. 10, pp. 895-902 (2009).
Nguyen et al., "Aryl Hydrocarbon Receptor Negatively Regulates Dendritic Cell Immunogenicity via a Kynurenine-Dependent Mechanism," *PNAS*, vol. 107, No. 46, pp. 19961-19966 (2010).
Opitz et al., "Tryptophan Degradation in Autoimmune Diseases," *Cell. Mol. Life Sci.*, vol. 64, pp. 2542-2563 (2007).
Opitz et al., "An endogenous tumour-promoting ligand of the human aryl hydrocarbon receptor," *Nature*, vol. 478, No. 7368, pp. 197-203 (2011).
Palermo et al., "Identification of Potential Aryl Hydrocarbon Receptor Antagonists in Green Tea," *Chem. Res. Toxicol.*, vol. 16, pp. 865-872 (2003).
Reyes et al., "Identification of the Ah Receptor Nuclear Translocator Protein (Arnt) as a Component of the DNA Binding Form of the Ah Receptor," *Science*, vol. 256, pp. 1193-1195 (1992).
Salmons et al., "Targeting of Retroviral Vectors for Gene Therapy," *Human Gene Therapy*, vol. 4, pp. 129-141 (1993).
Savouret et al., "7-Ketocholesterol Is an Endogenous Modulator for the Arylhydrocarbon Receptor," *The Journ. of Biological Chem.*, vol. 276, No. 5, pp. 3054-3059 (2001).
Tennant et al., "Targeting Metabolic Transformation for Cancer Therapy," *Nat. Rev. Cancer*, vol. 10, pp. 267-277 (2010).
Thackray et al., "Exploring the Mechanism of Tryptophan 2,3-dioxygenase," *Biochem Soc. Trans.*, vol. 36, pp. 1120-1123 (2008).
Trang et al., "MicroRNAs as Potential Cancer Therapeutics," *Oncogene*, vol. 27, pp. S52-S57 (2009).
Tsai et al., "Benzo[α]pyrene Regulates Osteoblast Proliferation through an Estrogen Receptor-Related Cyclooxygenase-2 Pathway," *Chem. Res. Toxicol.*, vol. 17, pp. 679-684 (2004).
Tuerk et al., "Systematic Evolution of Ligands by Exponential Enrichment: RNA Ligands to Bacteriophage T4 DNA Polymerase," *Science*, vol. 249, pp. 505-510 (1990).
Uyttenhove et al., "Evidence for a Tumoral Immune Resistance Mechanism based on Tryptophan Degradation by Indoleamine 2,3-dioxygenase," *Nat. Med.*, vol. 9, No. 10, pp. 1269-1274 (2003).
European Office Communication issued in related European Patent Application No. 12758452.2, dated Oct. 28, 2015.
Costantino, "New promises for manipulation of kynurenine pathway in cancer and neurological diseases," Expert Opinion in Therapeutic Targets, vol. 13, No. 2, pp. 247-258 (2009).
Casper et al., "Resveratrol Has Antagonists Activity on the Aryl Hydrocarbon Receptor: Implications for Prevention of Dioxin Toxicity," *The American Society for Pharmacology and Experimental Therapeutics*, vol. 56, pp. 784-790 (1999).
Japanese Notice of Reasons for Rejection issued in related Japanese Patent Application No. 2014-528990, issued Apr. 5, 2016.

\* cited by examiner

US 9,593,062 B2

MEANS AND METHODS FOR TREATING AND/OR PREVENTING NATURAL AHR LIGAND-DEPENDENT CANCER

CROSS-REFERENCE TO RELATED APPLICATION(S)

This application is a National Phase of PCT/EP2012/067504, filed Sep. 7, 2012, which claims priority from U.S. Provisional Patent Application No. 61/531,861, filed Sep. 7, 2011. The contents of these applications are incorporated herein by reference in their entirety.

The present invention relates to the field of cancer therapeutics and treatment of cancer. In particular, it relates to a method for treating and/or preventing a natural AHR ligand-dependent cancer comprising administering to a subject suffering from said cancer a therapeutically effective amount of an AHR inhibitor. Moreover, contemplated is a AHR inhibitor for use in treating and/or preventing a natural AHR ligand-dependent cancer.

Tumor micro-environment represents a particular challenge in an effective tumor therapy since it has multiple influences on the malignancy of a tumor (Tennant 2010, Nat Rev Cancer 10, 267).

Tryptophan (Trp) metabolism is an example for the importance of the tumor micro-environment. Its functional relevance as a pivotal endogenous mechanism for limiting the immune response has been demonstrated in animal models already (Munn 2007, J Clin Invest 117, 1147).

In particular, the activation of the Trp metabolism correlates with diseases and disorders of the immune system such as tumor immunity, autoimmunity, infectious diseases and maintenance of the immune privilege (Opitz 2007, Cell Mol Life Sci 64, 2452). Degradation of Trp by indoleamine-2,3-dioxygenases 1 and 2 (IDO1/2) in tumors and tumor draining lymph nodes inhibits antitumor immune responses and is associated with a poor prognosis in various malignancies (Lob 2009, Nat Rev Cancer 9 (6): 445) Inhibition of IDO1/2 suppresses tumor formation in animal models and is currently tested in phase I/II clinical trials in cancer patients (Muller 2005, Nat Med 11(3): 312, Uyttenhove 2003, Nat Med 9(10), 1269; DiPuccio 2010, Expert Opin Ther Pat 20, 229; Ball 2007, Gene 396(1), 203; Metz 2007, Cancer Res 67(15), 7082).

Another enzyme known to be involved in the Trp metabolism in neurons and hepatocytes is the tryptophan 2,3-dioxygenase (TDO) which synthesizes the first step of the Trp degradation as well (Thackray 2008, Biochem Soc Trans 36, 1120). TDO has also been reported as a potential target for tumor drugs (WO2010/008427) The relevance of Trp catabolism for human tumor formation and progression, however, remains elusive.

Kynurenin (Kyn) is a Trp metabolite having immunosupressive functions. However, its molecular targets and the mechanism how this effect is elicited is not yet understood. Exogenous Kyn has been reported to, inter alia, activate the Aryl-Hydrocarbon Receptor (AHR) transcription factor in dendritic cells and T-cells (Mezrich 2010, J Immunol 185, 3190; Nguyen 2010, Proc Natl. Acad Sci, USA, 107, 19961).

The AHR is a transcription factor of the basic helix-loop-helix (bHLH) Per-Arnt-Sim (PAS) family, which is activated by xenobiotics such as benzoapyrene and 2,3,7,8-tetrachlordibenzodioxin (TCDD). In the nucleus the AHR forms a heterodimer with the AHR nuclear translocator (ARNT) that interacts with the core binding motif of the dioxin-responsive elements (DRE) located in regulatory regions of AHR target genes (Reyes 1992, Science 256, 5060; Abel 2010, Biol Chem 391, 1235).

AHR is known to be involved into chemical carcinogenesis elicited by, e.g., halogenated aromatic hydrocarbons. Further, it has been reported that green tea extracts can act as antagonists of the AHR and, thereby, can prevent the harmful effects of such halogenated aromatic hydrocarbons (Palermo 2003, Chem Res Toxicol 16, 865). Moreover, constitutive expression of the AHR gene is known to be involved in cellular survival in glioblastoma cells (Gramatzki 2009, Oncogene 28, 2593).

In light of the above, the provision of means and methods for effectively treating tumors the malignancy of which are dependent on metabolic processes such as the Trp catabolism are not yet available but would be nevertheless highly desirable.

SUMMARY OF THE INVENTION

The present invention relates to a method for treating and/or preventing a natural AHR ligand-dependent cancer comprising administering to a subject suffering from said cancer a therapeutically effective amount of an AHR inhibitor.

In a preferred embodiment of the method of the invention, said cancer is selected from the group consisting of: brain tumors, preferably, glioma, melanoma, colorectal adenocarcinoma, colon carcinoma, renal cell carcinoma, NSCLC, breast cancer, hepatocellular carcinoma, ovarian carcinoma, head and neck carcinoma, bladder cancer, pancreatic adenocarcinoma, mesothelioma, and SCLC.

In a preferred embodiment of the method of the invention, said AHR inhibitor is a small molecule compound.

In a more preferred embodiment of the method of the invention, said small molecule compound is a plant compound or derivative thereof.

In a more preferred embodiment of the method of the invention, said plant compound or derivative thereof is a flavone or derivative thereof. Most preferably, said flavone or derivative thereof is 3,4-dimethoxyflavone, 3'-methoxy-4'-nitroflavone, 4',5,7-Trihydroxyflavone (apigenin), or 1-Methyl-N-[2-methyl-4-[2-(2-methylphenyl)diazenyl]phenyl-1H-pyrazole-5-carboxamide (CH223191; CAS number 301326-22-7).

In another more preferred embodiment of the method of the invention, said plant compound or derivative thereof is reveratrol or a derivative thereof, epigallocatechin or epigallocatechingallate.

In another preferred embodiment of the method of the invention, said small molecule compound is a compound characterized by the following general formula (I):

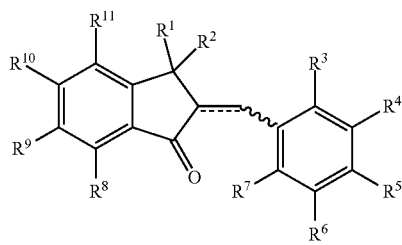

wherein
(i) $R^1$ and $R^2$ independently of each other are hydrogen or a $C_1$ to $C_{12}$ alkyl, (ii) $R^3$ to $R^{11}$ independently from each other are hydrogen, a $C_1$ to $C_{12}$ alkyl, hydroxyl or a $C_1$ to $C_{12}$ alkoxy, and (iii) the broken line represents either a double bond or two hydrogens.

In another preferred embodiment of the method of the invention, said AHR inhibitor is an antibody which specifically binds to and inhibits the AHR protein.

In another preferred embodiment of the method of the invention, said AHR inhibitor is the AHR repressor protein or an inactive AHR nuclear translocator (ARNT).

In another preferred embodiment of the method of the invention, said AHR inhibitor is a nucleic acid inhibitor.

In another more preferred embodiment of the method of the invention, said nucleic acid repressor specifically binds to an AHR encoding polynucleotide and is selected from the group consisting of: a ribozyme, an antisense molecule, an inhibitors oligonucleotide, a micro RNA, and an siRNA.

Moreover, contemplated by the invention is an AHR inhibitor for use in treating and/or preventing a natural AHR ligand-dependent cancer.

FIGURES

FIG. 1 shows that TDO degrades Trp to Kyn in human brain tumors. a, Trp (left) and Kyn (right) content in the supernatants of human astrocytes (hAs), glioma cell lines and GIC (T323) cultured for 72 h and measured by HPLC (n=4). b, Correlation between TDO mRNA and Kyn release of human glioma cells measured by quantitative RT-PCR and HPLC (n=4). c, Kyn concentrations in the supernatants of U87 glioma cells cultured for 48 h in the presence of the TDO inhibitor 680C91 (black bars) or its solvent (white bars; n=4, P=0.005, 0.002 and 0.0009 for 1, 5 and 10 µM TDOI, respectively). d, Kyn release of glioma cells after knockdown of TDO (black bars, P=0.000007, 0.0007 and 0.00006, respectively), IDO1 (dark gray bars) or IDO2 (light gray bars) by siRNA (n=3). e, Weak neuronal TDO expression in healthy brain tissue (upper panel). TDO expression in glioblastoma (WHO grade IV, lower panel); red: TDO staining; * necrosis; arrowheads: border to infiltrated brain tissue. Inset: single tumor cells (arrows) infiltrating the adjacent brain tissue. Magnification: 40×, insets 400× (upper panel), 100× (lower panel). f, Plot of TDO expression [H-score] in brain tumors of increasing malignancy (WHO grade II-IV; grade II, n=18, grade III, n=15, grade IV, n=35). g, Correlation of the Ki-67 proliferative index with the TDO H-score in gliomas of different WHO grades (n=42). h, Trp (left) and Kyn (right) concentrations in the sera of 24 glioblastoma patients and 24 age- and sex-matched healthy controls, measured by HPLC. i, Quantification of quinolinic acid staining in healthy human brain tissue (white bar, n=5) and glioblastoma tissue (black bar, n=5). The data distribution in (f) and (g) is presented as box plots, showing the 25th and 75th percentile together with the median, whiskers represent the 10th and 90th percentile, respectively.

Figure 2:
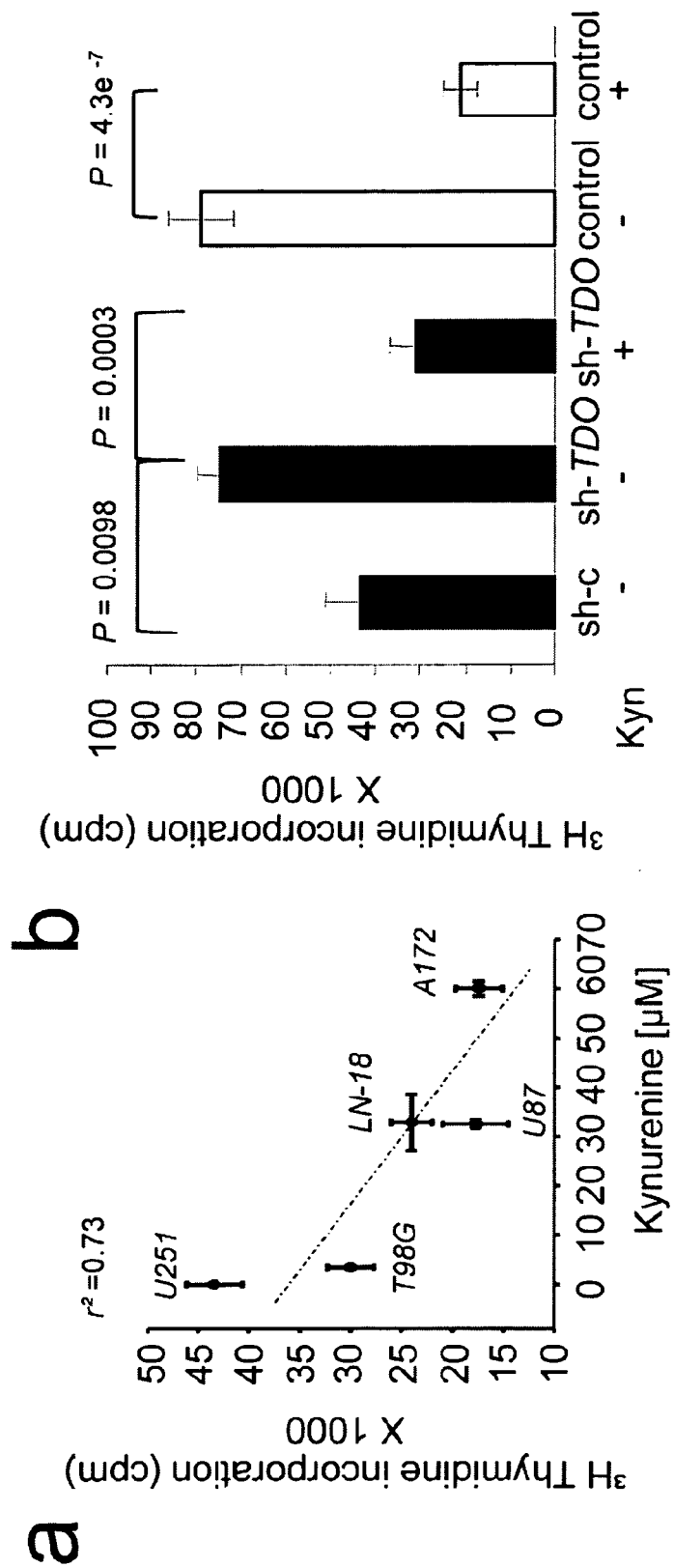
Figure 2:
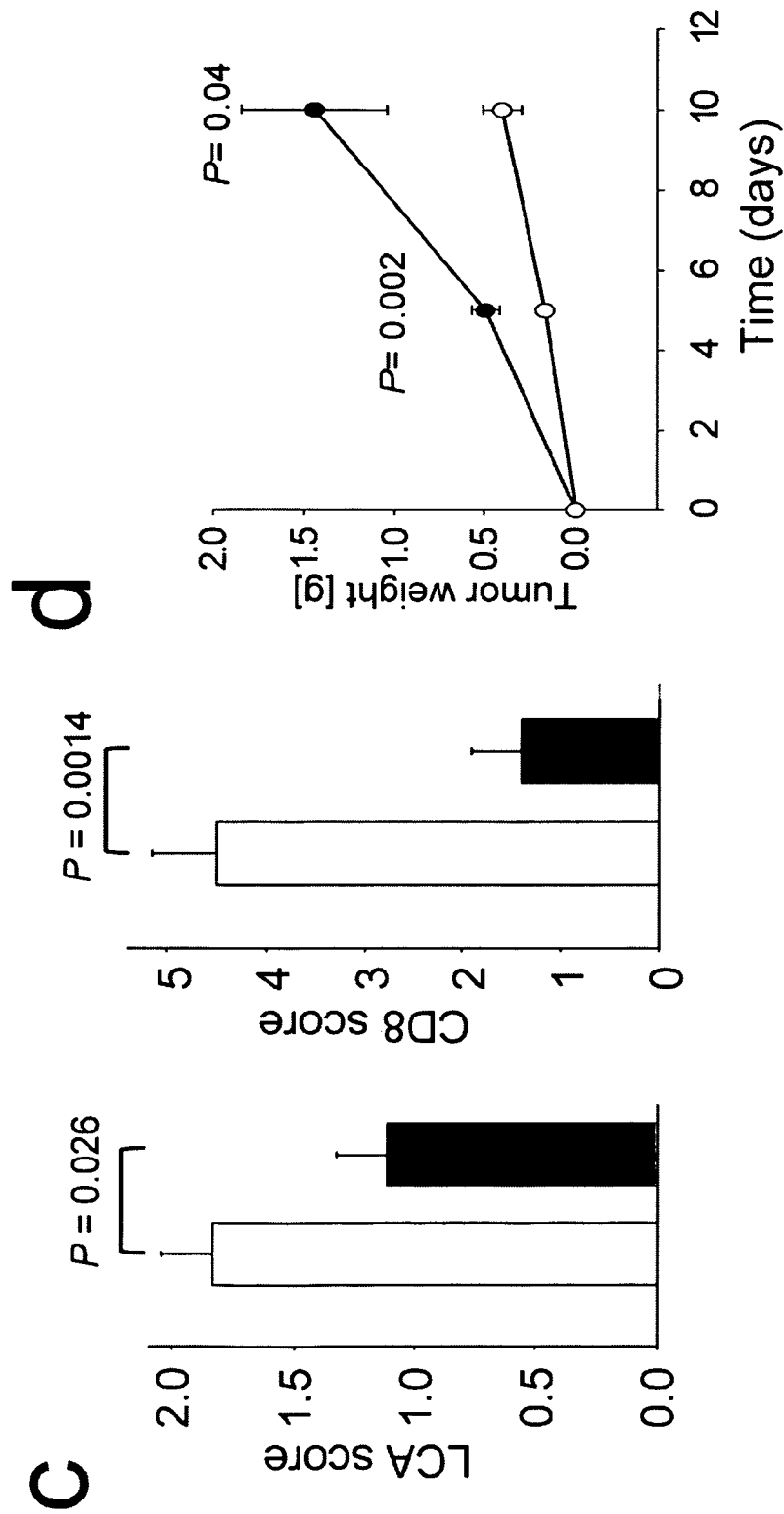
Figure 2:
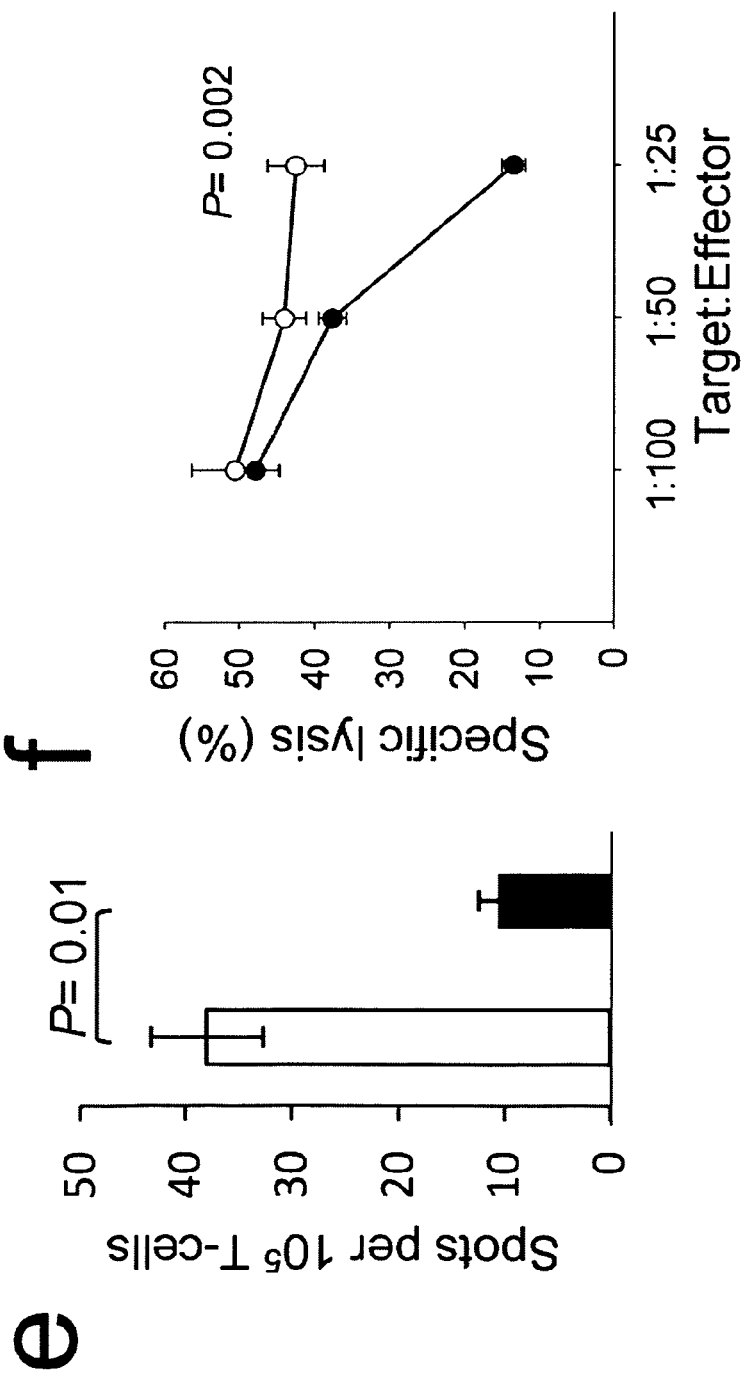
Figure 2:
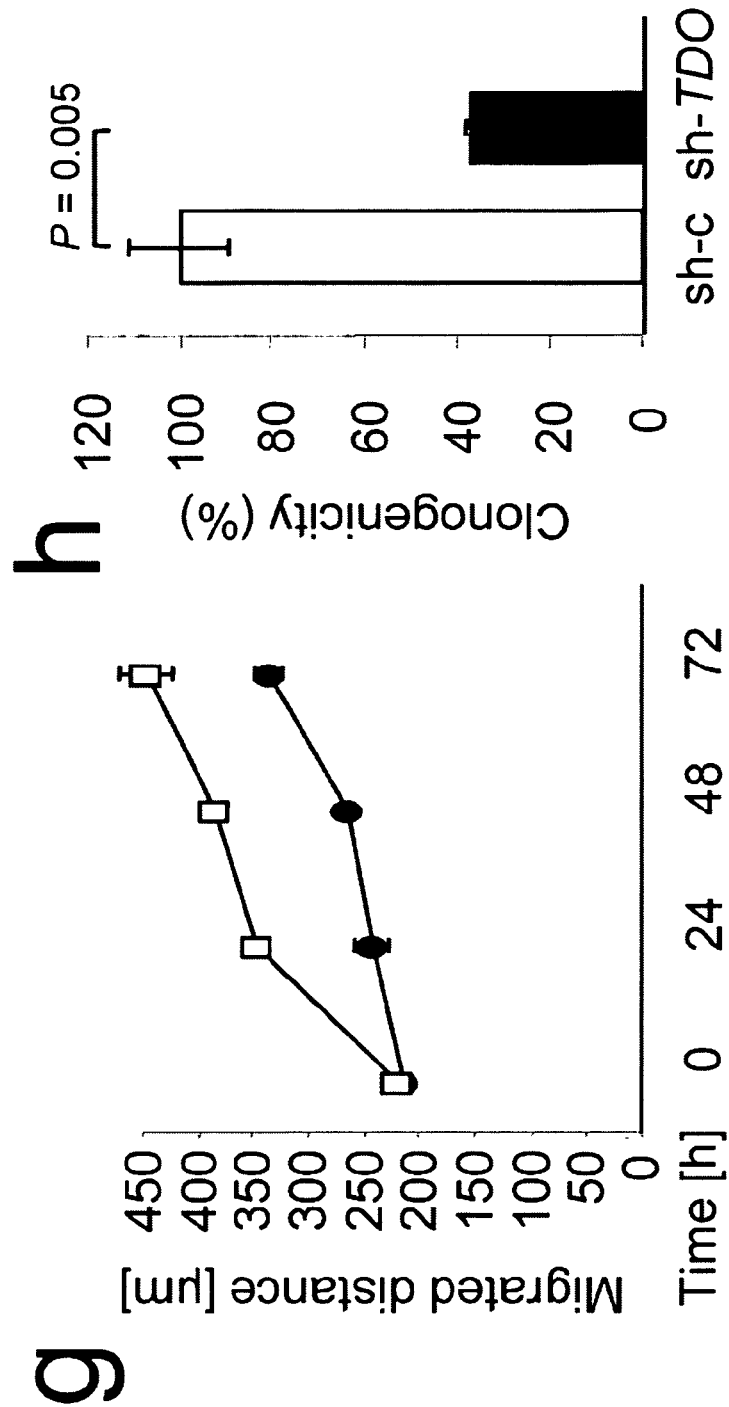
Figure 2:
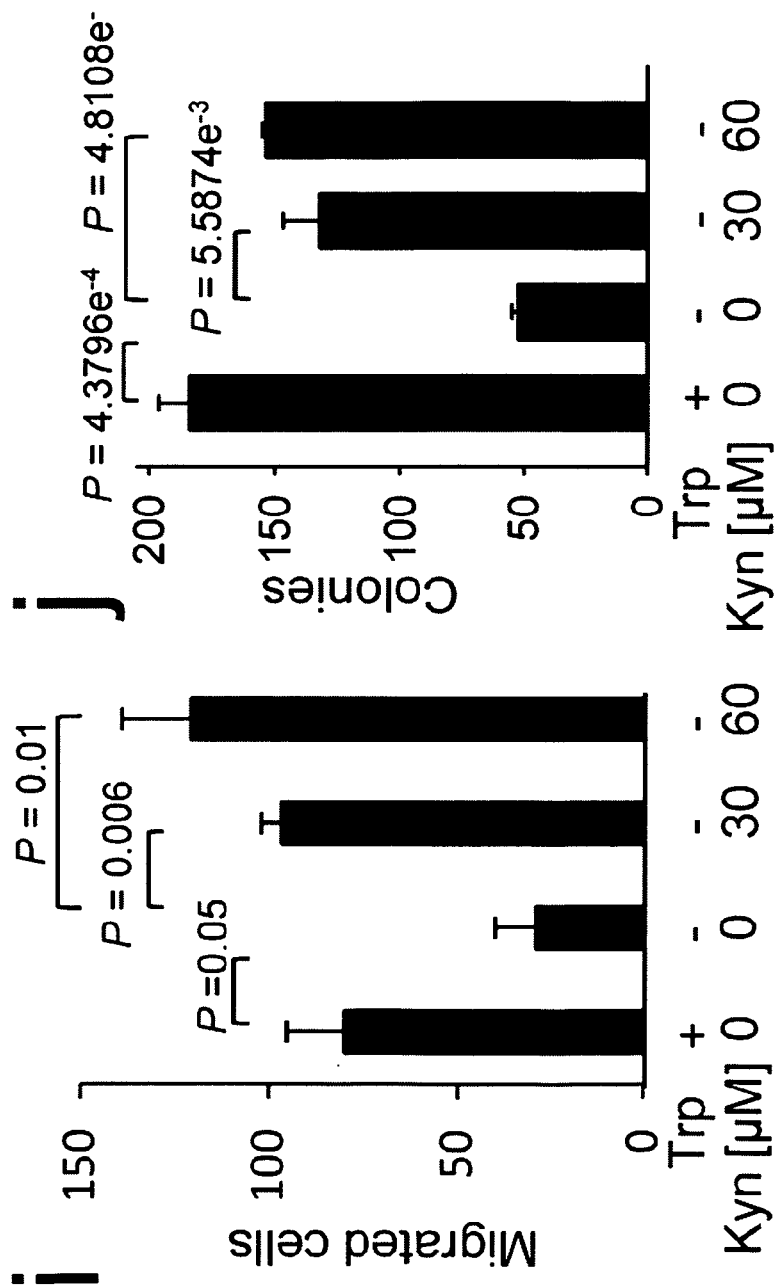
Figure 2:
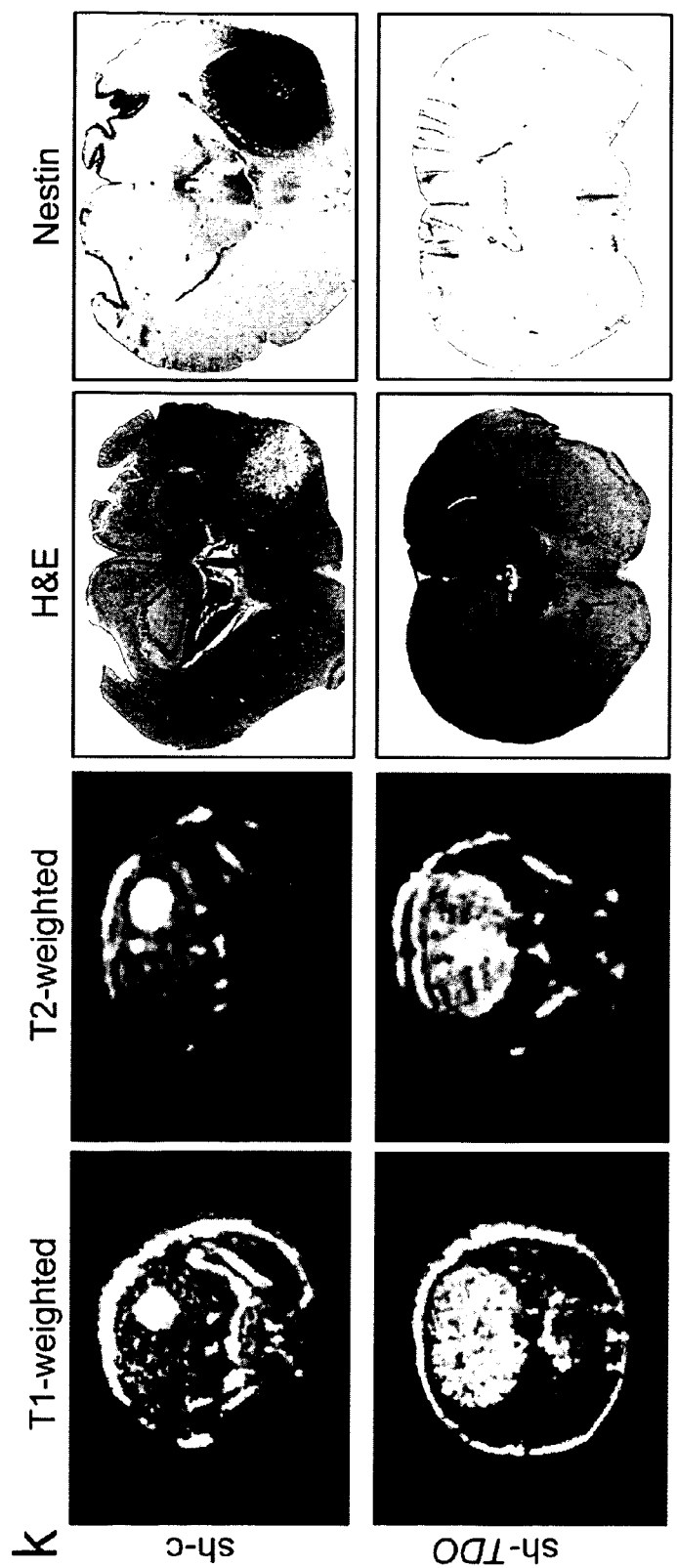
Figure 2:
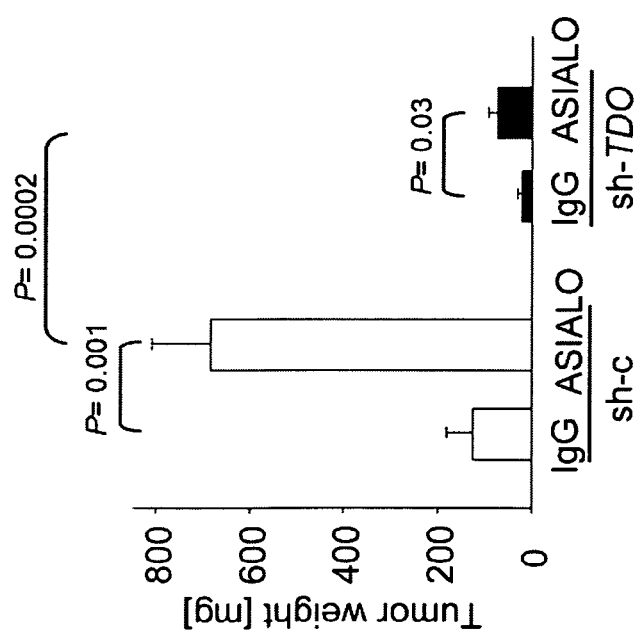

FIG. 2 shows paracrine effects of TDO-mediated Kyn release by glioma cells on immune cells. a, Correlation of the allogeneic proliferation of PBMC cocultured with different glioma cell lines with the Kyn release of the glioma cells (n=3). b, Allogeneic proliferation of PBMC cocultured with TDO-expressing control U87 glioma cells (sh-c) in comparison to U87 glioma cells with a stable short hairpin RNA-mediated knockdown of TDO (sh-TDO), with or without 100 µM Kyn (black bars), in comparison to PBMC alone with or without 100 µM Kyn (white bars, n=3). c, Quantification of LCA+ cells (left graph) and CD8+ cells (right graph) stained in human glioma sections with low TDO expression (H-score<150, white bar, n=12 for LCA, n=10 for CD8) and in human glioma sections with high TDO expression (Hscore≥150, black bar, n=17 for LCA and n=10 for CD8). d, Growth of Tdo-deficient GL261 murine glioma cells stably transfected with Tdo (solid circles) or empty vector (open circles) injected s.c. into the flank of C57BL/6N mice was monitored using metric callipers (n=6). Tumor weight was calculated using the equation: tumor weight (g)=(length (cm)×width (cm)2)×0.5. e, IFN-γ-release of T cells of mice bearing subcutaneous Tdo-expressing tumors (black bar) in comparison to T cells of mice bearing Tdo-deficient tumors (white bar) after restimulation with glioma lysates measured by ELISpot (n=3). f, Lysis of GL261 murine glioma cells by spleen cells of mice with Tdo-expressing GL261 tumors in comparison to those with a subcutaneous Tdo-deficient GL261 tumors measured by chromium release (n=4). g, Quantification of the migrated distances of sh-c (open squares) and sh-TDO (solid circles) cells into a collagen matrix (n=3, P=0.004, 0.0005 and 0.01 for 24, 48 and 72 h, respectively). h, Clonogenic survival of sh-c (white bar) and sh-TDO (black bar) U87 cells (n=3). i, Matrigel boyden chamber assay of U87 glioma cells in the absence or presence of 70 µM Trp without or with 30 µM or 60 µM Kyn (n=3). j, Clonogenic survival of LN-18 glioma cells in the absence or presence of 70 µM Trp without or with 30 µM or 60 µM Kyn (n=3). k, Representative cranial MRIs, H&E and nestin stainings of CD1 nu/nu mice implanted with sh-c (upper panel) or sh-TDO (lower panel) U87 glioma cells. The images are representative of two independent experiments (n=6). l, Tumor weight of sh-c (white bars) and sh-TDO (black bars) U87 glioma cells injected s.c. in the flank of CD1 nu/nu mice, that were treated either with anti-asialo GM1 antibody (ASIALO) for NK cell depletion or control IgG (IgG) (n=8).

Figure 3:
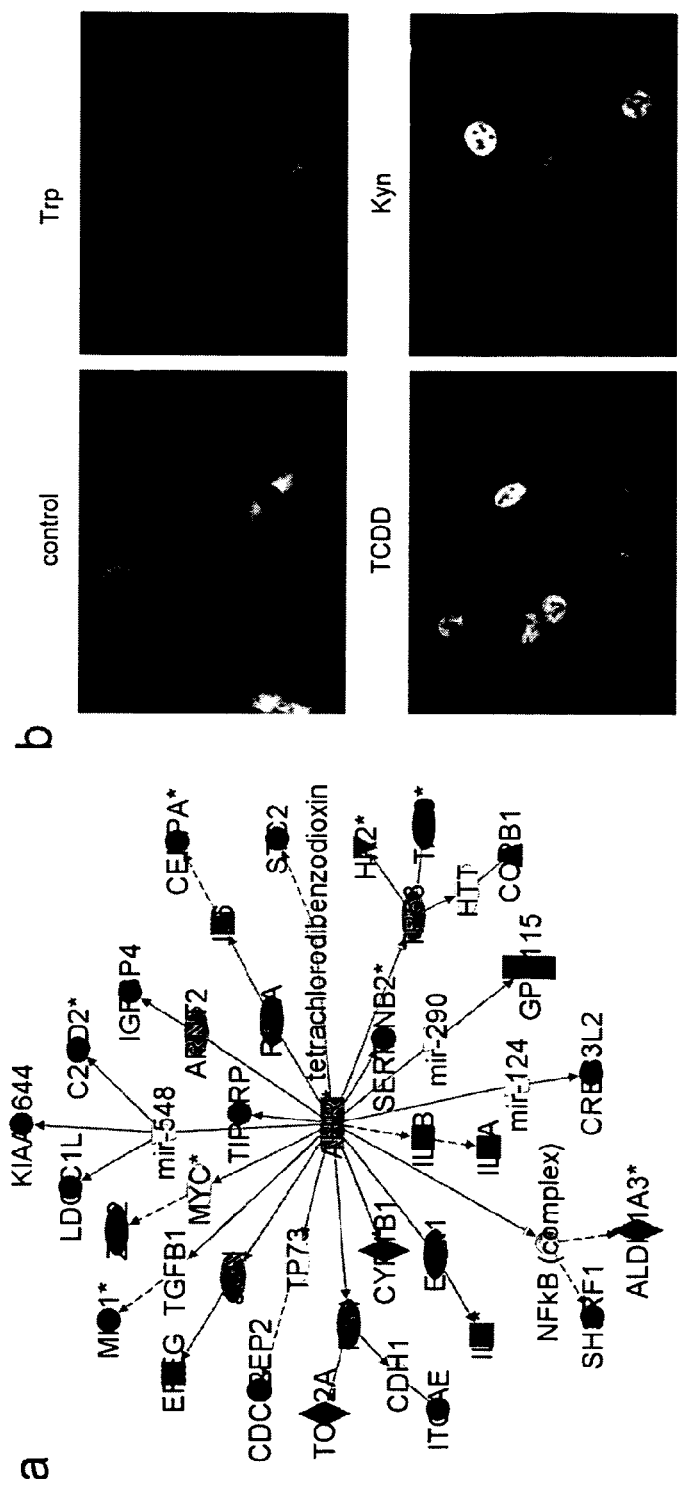
Figure 3:
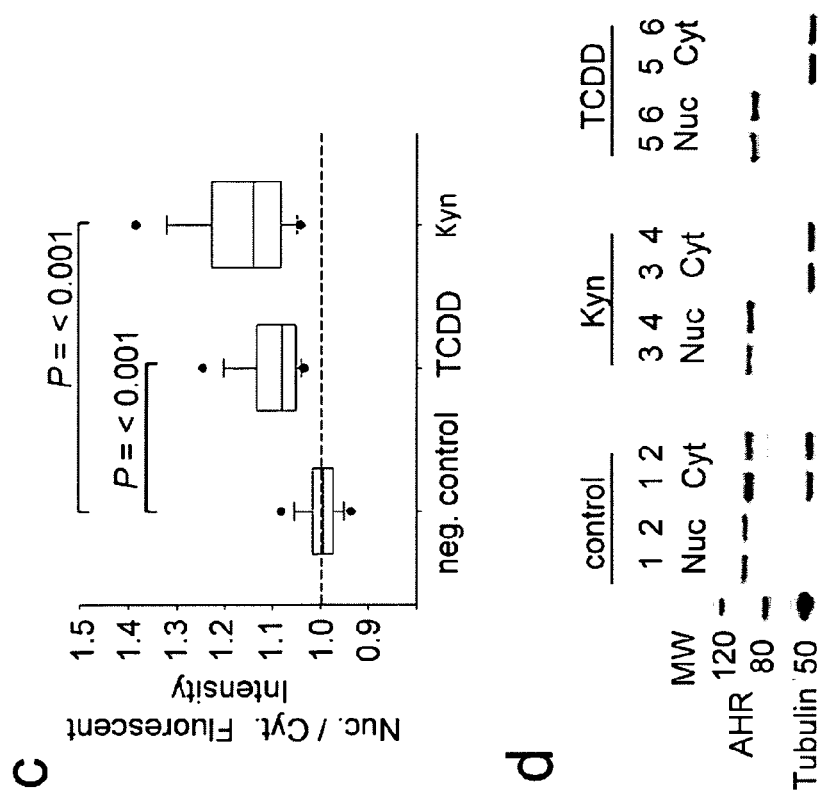
Figure 3:
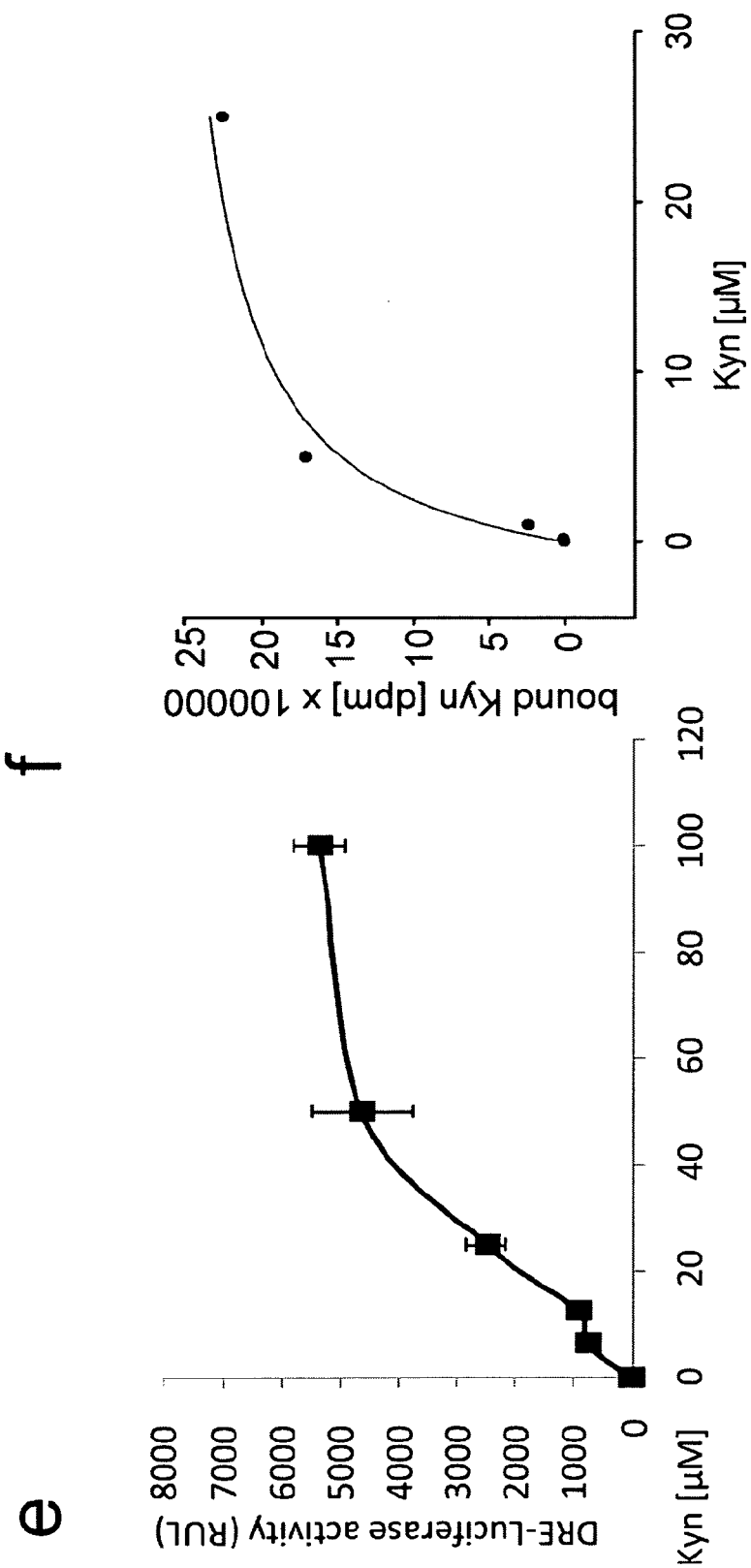
Figure 3:
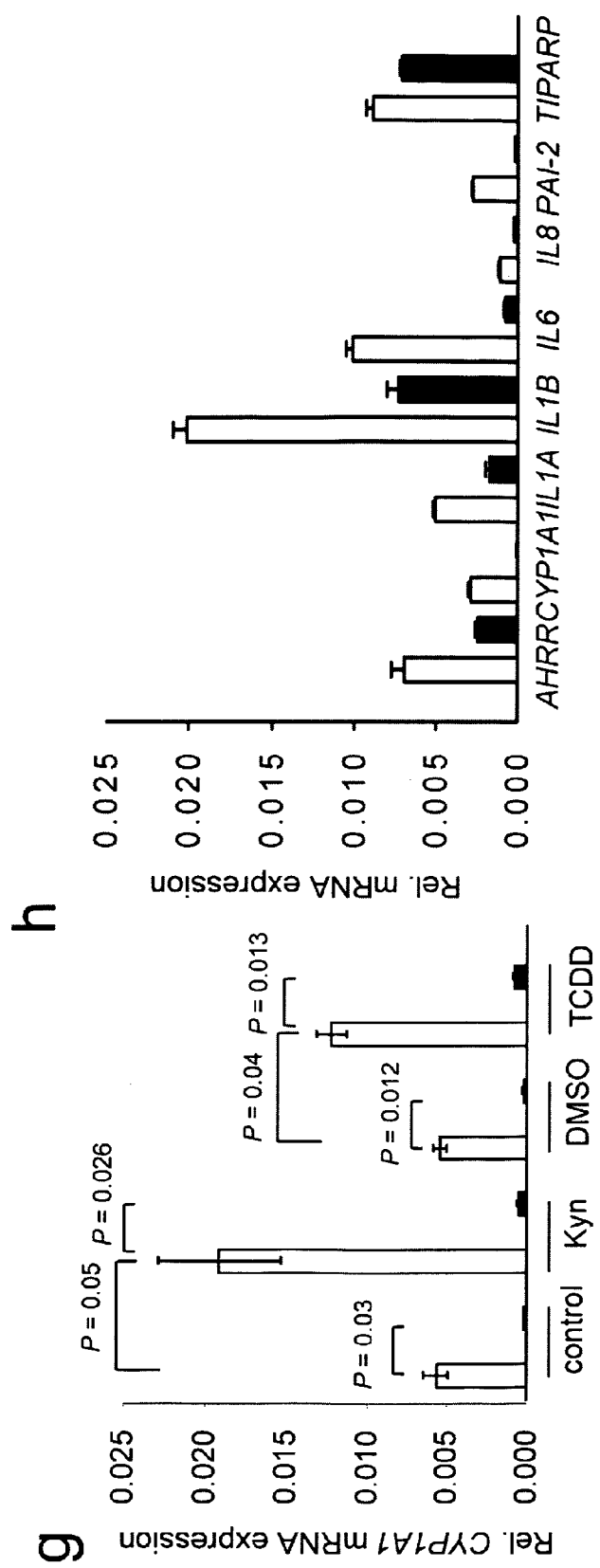

FIG. 3 shows that Kyn activates the AHR. a, Connection of the 25 genes that were most strongly induced by Kyn treatment in U87 cells after 8 h to AHR signaling (red: upregulation, green: downregulation). b, Translocation of GFP-tagged AHR into the nucleus of mouse hepatoma cells, which do not degrade Trp, after 3 h treatment with 50 µM Kyn, 50 µM Trp or 1 nM TCDD (neg. control: medium). c, Ratios of nuclear to cytoplasmic fluorescent intensity in cells with GFP-tagged AHR after 3 h of indicated treatment (neg. control: medium, pos. control: 1 nM TCDD, 50 µM Kyn). The data distribution is represented by box plots, showing the 25th and 75th percentile together with the median, whiskers represent the 10th and 90th percentile, respectively (P<0.001, one way ANOVA on ranks, followed by Dunns' method). d, AHR Western blots of two different nuclear and cytoplasmic fractions each of control (1,2), Kyn-treated (3,4) and TCDD-treated (5,6) human LN-229 glioma cells. e, Dioxinresponsive element (DRE) chemical activated luciferase gene expression in U87 glioma cells treated with indicated Kyn concentrations (n=2). f, Radioligand binding assay with indicated concentrations of L-3H-Kyn using mouse liver cytosol from Ahr-proficient and Ahr-deficient mice. Specific binding was calculated by subtracting the radioactivity measured in Ahrdeficient cytosol from that of Ahr-proficient cytosol (n=4) g, CYP1A1 mRNA expression in sh-AHR LN-308 glioma cells (black bars) in comparison to controls (sh-c, white bars) treated with 100 µM Kyn, 1 nM TCDD or controls (n=4). h, mRNA expression of AHR target genes in sh-TDO (black bars) in comparison to sh-c U87 glioma cells (white bars, n=4).

Figure 4:
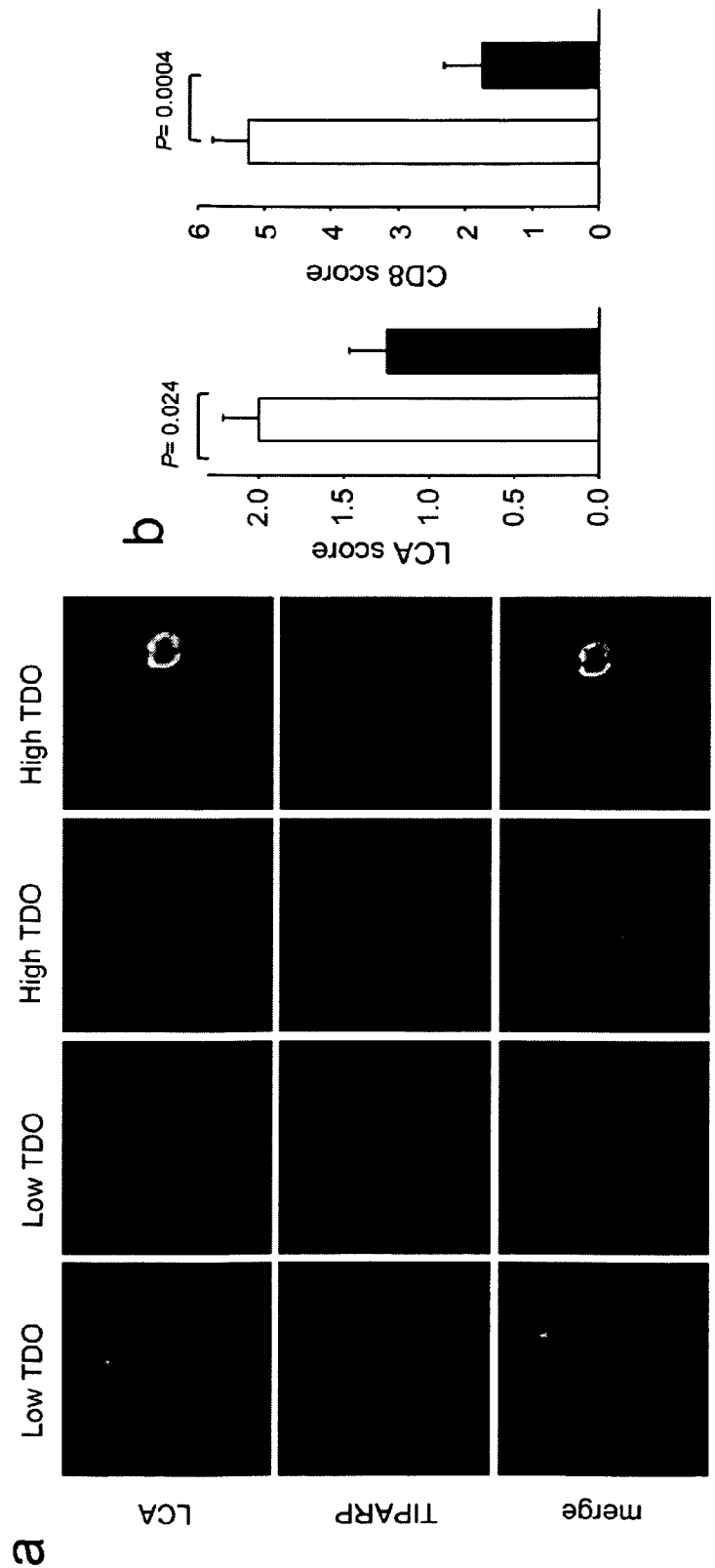
Figure 4:
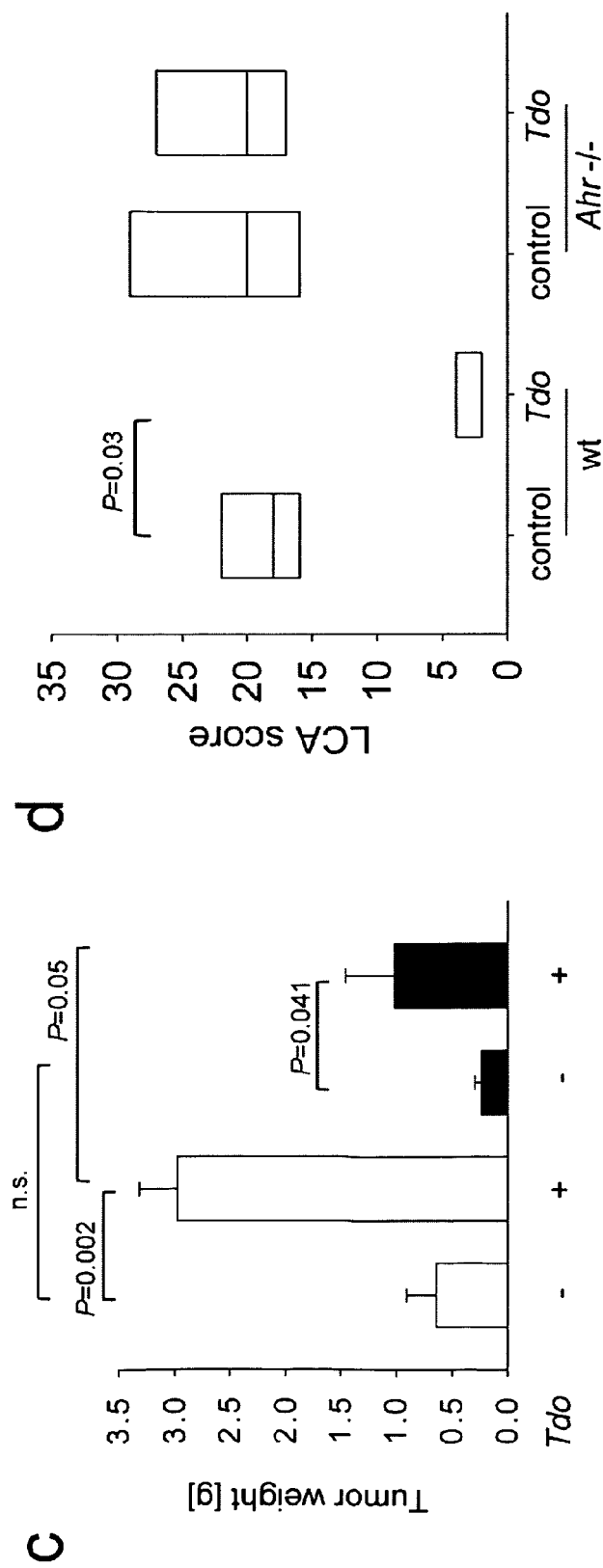
Figure 4:
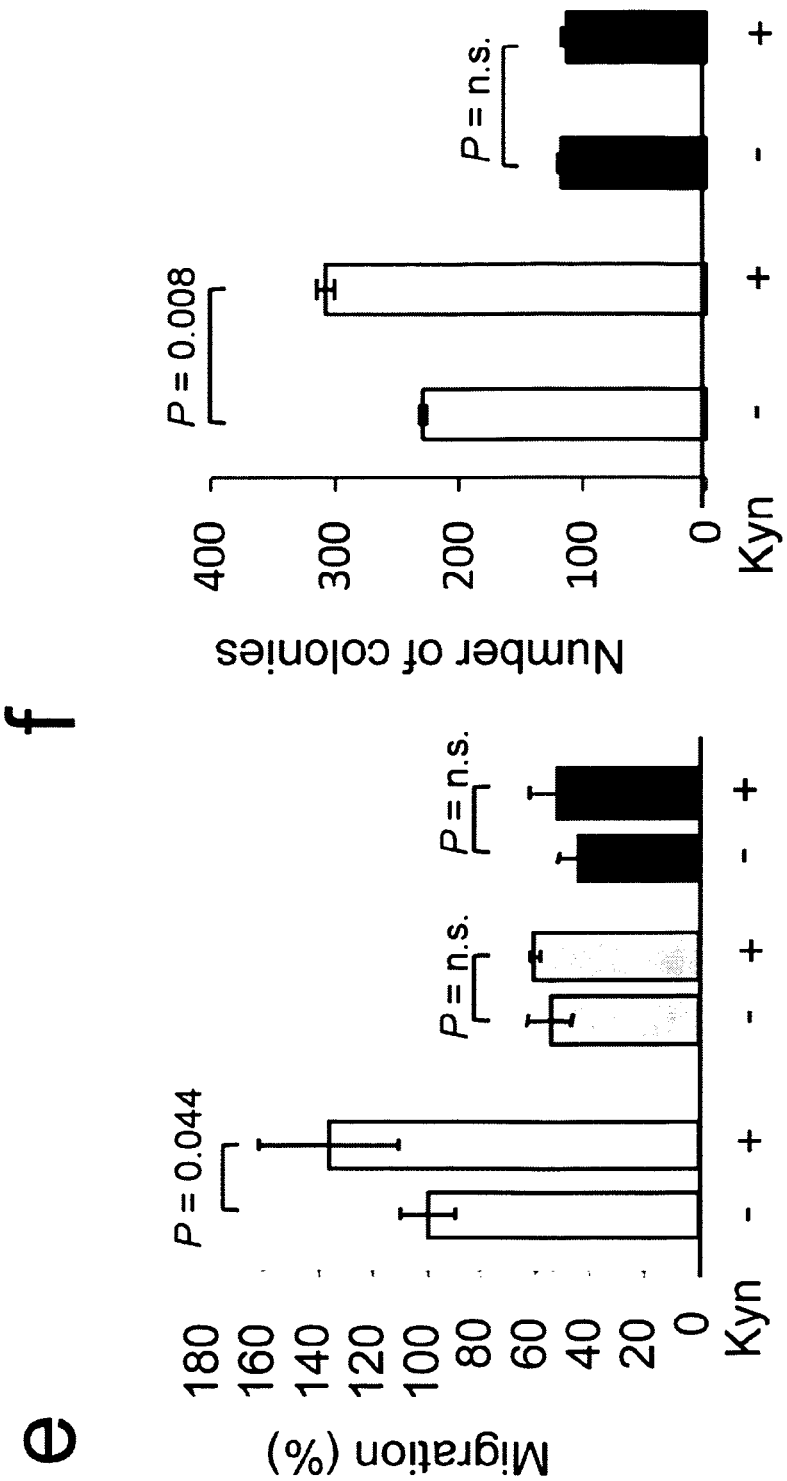
Figure 4:
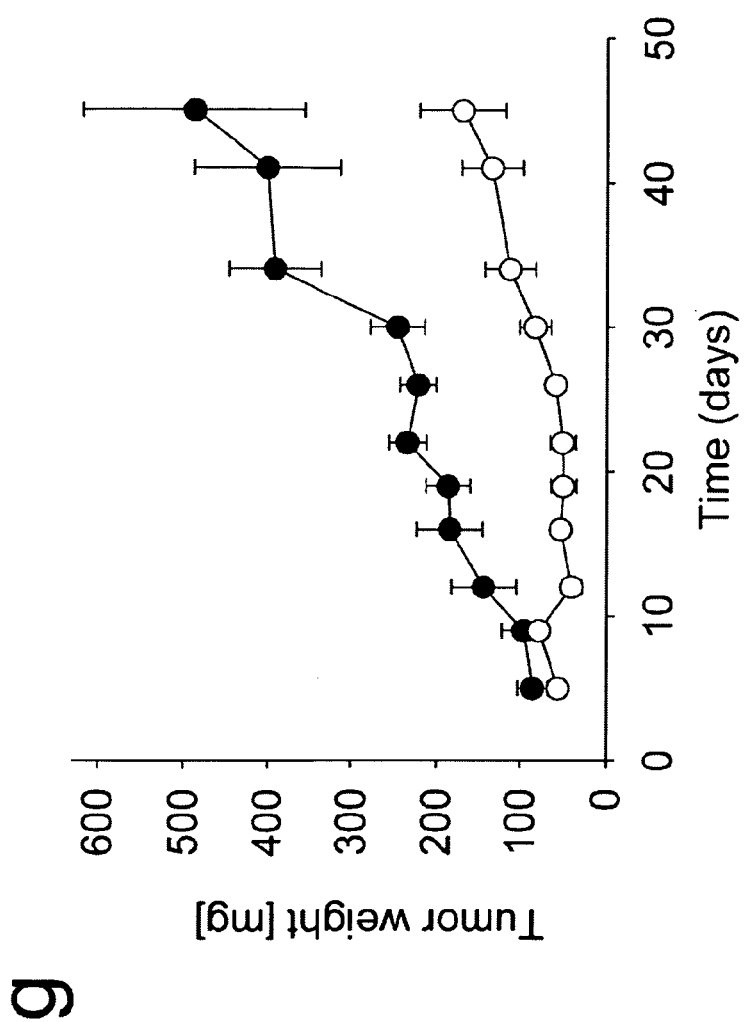

FIG. 4 shows that the autocrine and paracrine effects of TDO-derived Kyn are mediated via the AHR a, Immunofluorescence stainings of LCA and TIPARP in human glioma sections with low or high TDO expression. Magnification: 400×. b, Quantification of LCA+ cells (left) and CD8+ cells (right) stained in human glioma sections with low AHR expression (Histoscore<150, white bar, n=10 for LCA and n=8 for CD8) and in human glioma sections with high AHR expression (Histoscore≥150, black bar, n=12 for LCA and n=12 for CD8. c, Tumor weight measured 15 days after s.c. injection of murine GL261 glioma cells with and without Tdo expression in the flanks of Ahr-proficient (white bars) or Ahr-deficient mice (black bars, n=6). d, Quantification of LCA+ immune cells stained in the subcutaneous Tdo-proficient and Tdodeficient GL261 tumors in Ahr-proficient and Ahr-deficient mice presented as box plots, showing the 25th and 75th percentile and the median (n=4). e, Migration of sh-c LN-308 glioma cells (white bars) and LN-308 glioma cells with knockdown of the AHR by two different shRNAs (sh-AHR1, gray bars and sh-AHR2 black bars) in the presence or absence of 100 µM Kyn (n=4). f, Clonogenicity of sh-c (white bars) and sh-AHR (black bars) LN-308 glioma cells with or without 100 µM Kyn (n=3). g, Growth of AHR-proficient (solid circles) and AHR-deficient (open circles) human LN-308 glioma cells injected s.c. into the flank of CD1nu/nu mice was monitored using metric callipers (n=7). Tumor weight was calculated using the equation: tumor weight (g)=(length (cm)×width (cm)2)×0.5.

Figure 5:
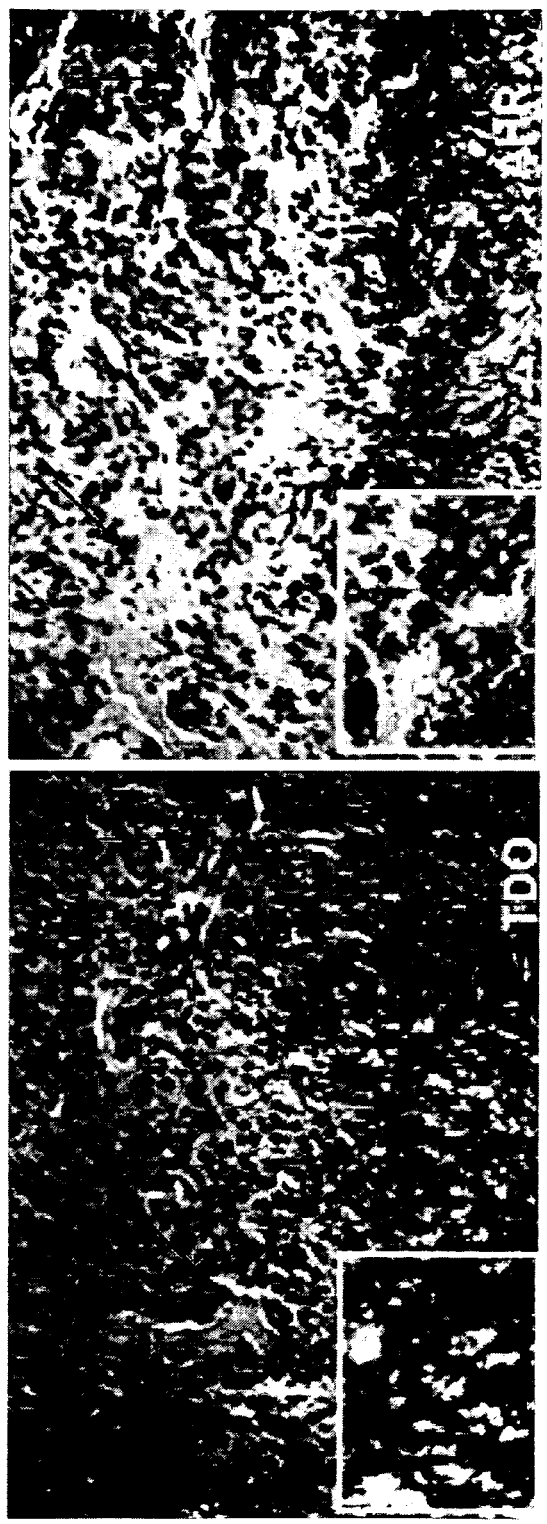
Figure 5:
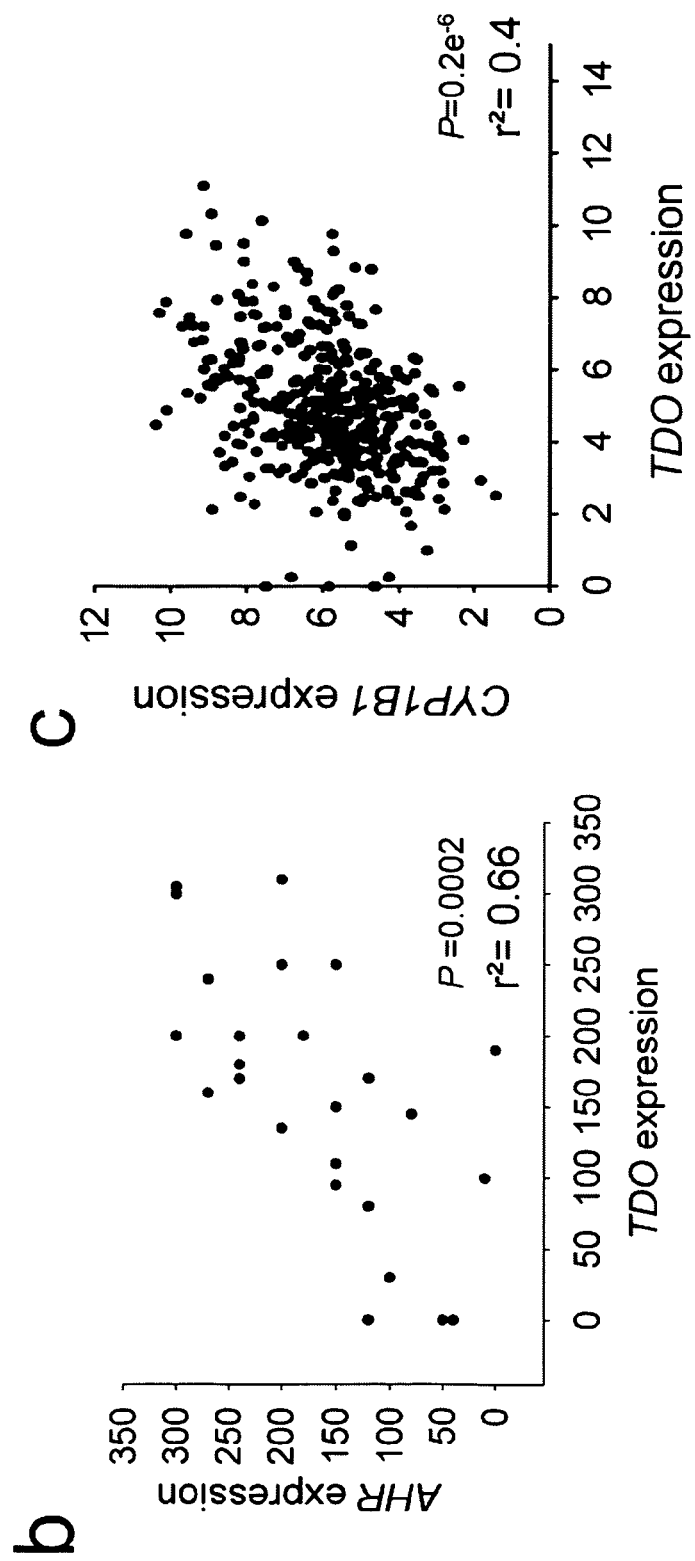
Figure 5:
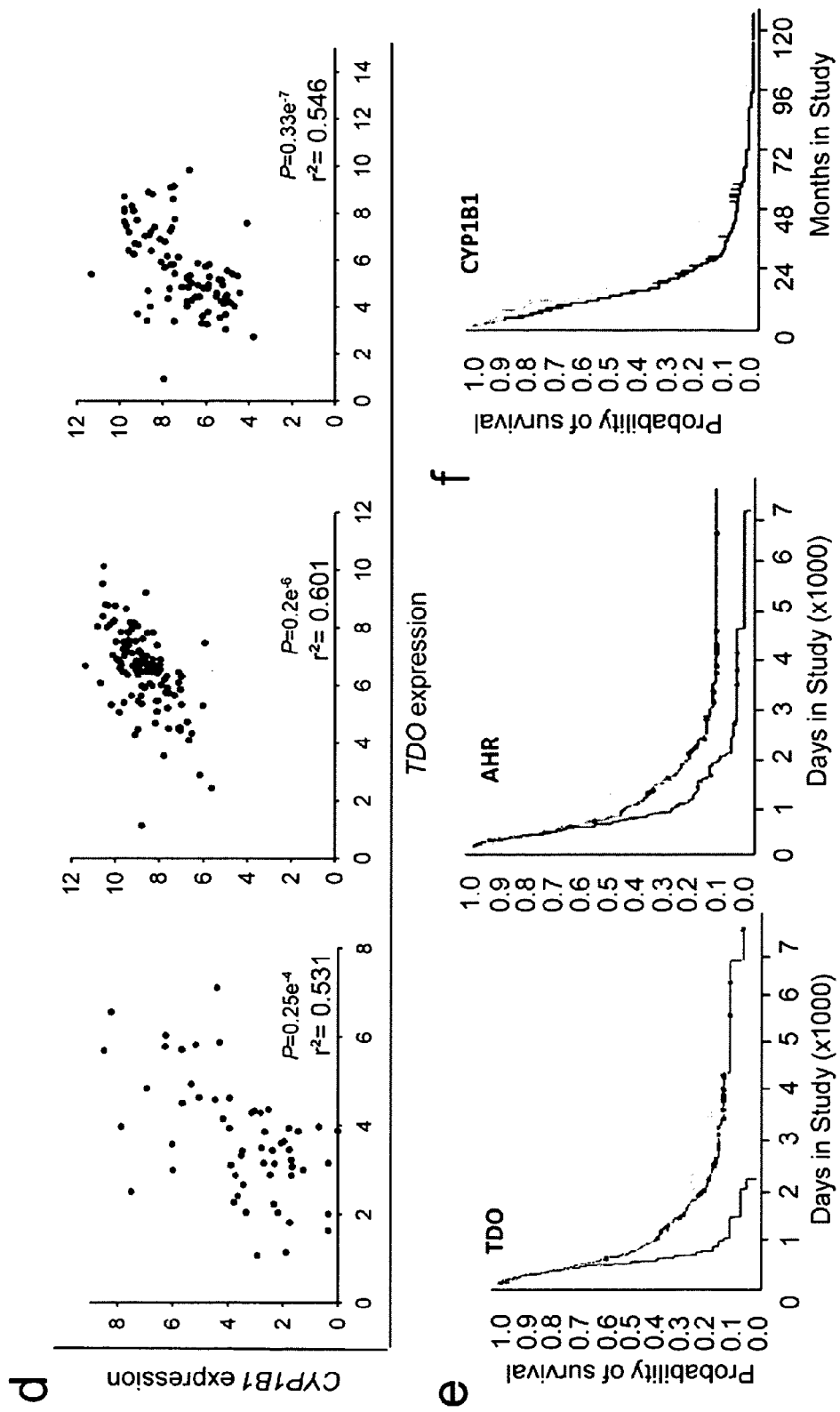
Figure 5:
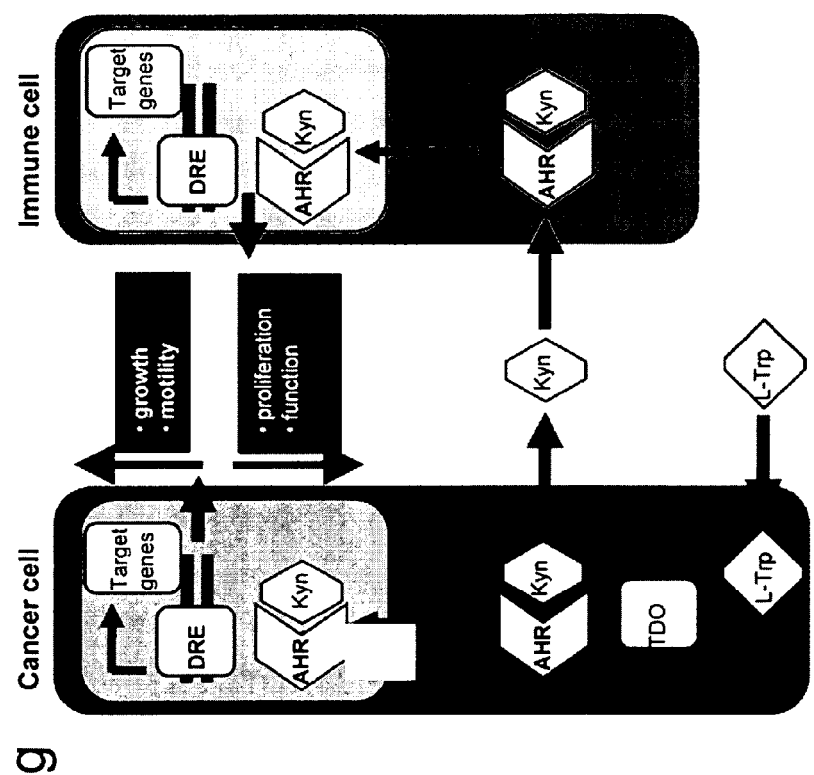

FIG. 5 shows that TDO-derived Kyn activates the AHR in diverse human cancers and AHR activation predicts survival in glioma patients a, Correlation of TDO expression (red) and AHR expression (brown) in consecutive sections of human glioblastoma tissue. Arrows indicate vessels for orientation. Magnification 40×, insets 200×. b, Correlation between TDO and AHR expression in human glioma tissue based on H-scores of TDO and AHR, calculated using Spearman rank correlation (n=26). c, Correlation between TDO and CYP1B1 expression in microarray data of human glioblastoma (n=396) analysed by Spearman rank correlation. d, Correlation between TDO and CYP1B1 expression in microarray data of human bladder cancer (left, n=58), human lung cancer (middle, n=122) and human ovarian carcinoma (right, n=91) analysed by Spearman rank correlation. e, Survival probabilities of glioma patients (WHO grade II-IV) with high expression (red) of TDO or the AHR compared to patients with intermediate (blue) or low (green) expression of these genes derived from Rembrandt. For statistical analysis see Supplementary note 21. f, Survival probabilities of glioblastoma patients with high expression (red) of the AHR target gene CYP1B1 compared to patients with low (green) expression of CYP1B1 derived from the glioblastoma data set of The Cancer Genome Atlas (TCGA) network (n=362). g, Synoptical figure highlighting the autocrine and paracrine effects of TDO-derived Kyn on cancer cells and immune cells via the AHR.

DETAILED DESCRIPTION OF THE INVENTION

The present invention relates to a method for treating and/or preventing natural AHR ligand-dependent cancer comprising administering to a subject suffering from said cancer a therapeutically effective amount of an AHR inhibitor.

The term "treating" as used herein refers to any improvement of the cancer that occurs in a treated subject compared to an untreated subject. Such an improvement can be a prevention of a worsening or progression of the cancer. Moreover, such an improvement may also be an amelioration or cure of the cancer or its accompanying symptoms. It will be understood that a treatment may not be successful for 100% of the subjects to be treated. The term, however, requires that the treatment is successful for a statistically significant portion of the subjects (e.g. a cohort in a cohort study). Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.05, 0.01, 0.005, or 0.0001.

The term "preventing" as used herein refers to avoiding the onset of cancer as used herein or its accompanying syndromes. It will be understood that prevention refers to avoiding the onset of cancer within a certain time window in the future. Said time window shall, preferably, start upon administration of a compound in the sense of the invention and lasts for at least 1 month, at least 6 months, at least 9 months, at least 1 year, at least 2 years, at least 5 years, at least 10 years or even for the remaining physiological life span of a subject. It will be understood that a prevention may not be successful for 100% of the subjects to be treated. The term, however, requires that the prevention is successful for a statistically significant portion of the subjects (e.g. a cohort in a cohort study). Whether a portion is statistically significant can be determined without further ado by the person skilled in the art using various well known statistic evaluation tools discussed also elsewhere herein in detail.

The term "natural AHR ligand-dependent cancer" as used herein refers to any malignant neoplasm which is dependent on the constitutive activation of AHR elicited by a natural AHR ligand. Preferably, said natural AHR ligand is kynurenin (Kyn). Kynurenin is, preferably, produced by tryptophan degradation as a consequence of increased expression of tryptophan degrading enzymes. More preferably, the cancer according to the invention is, thus, cancer associated with increased tryptophan-2,3-dioxygenase (TDO) activity. TDO activity as referred to herein can be, preferably, assessed by measuring the kynurenin and/or tryptophan concentrations present in a cancer tissue or cancer cells. Moreover, increased TDO activity can also be assessed by determining the amount of TDO enzyme or transcripts encoding said TDO enzyme in a cancer tissue or cancer cells. The amount of TDO enzyme can be determined by antibody-based techniques, such as ELISA, while the amount of transcripts can be determined by nucleic acid hybridization techniques, such as Northern blots, or by nucleic acid amplification techniques, such as RT-PCR. Particular preferred techniques for determining whether there is increased TDO associated with a cancer are described in the accompanying Examples, below, or are disclosed in WO2010/008427, the respective disclosure content of which is herewith incorporated by reference. Preferably, said aforementioned cancer is selected from the group consisting of: brain tumors, preferably, glioma, melanoma, colorectal adenocarcinoma, colon carcinoma, renal cell carcinoma, non-small cell lung cancer (NSCLC), breast cancer, hepatocellular carcinoma, ovarian carcinoma, head and neck carcinoma, bladder cancer, pancreatic adenocarcinoma, mesothelioma, and small cell lung cancer (SCLC). Alternatively, and also more preferably, the cancer according to the invention is, thus, cancer associated with increased indoleamine-2,3-dioxygenase 1 or 2 (IDO1 or 2) activity. Preferred cancers envisaged in this context are well known in the art; see, e.g., Lob 2009, Nat Rev Cancer 9(6), 445, the respective disclosure content of which is herewith incorporated by reference.

An "AHR inhibitor" in the sense of the invention is a compound capable of inhibiting either directly or indirectly the activity of the Aryl-Hydrocarbon Receptor (AHR) Polypeptide. The AHR polypeptide as referred to in accordance with the present invention is a member of the family of basic-helix-loop-helix transcription factors. It is a cytosolic transcription factor that is normally inactive and present in a complex with several chaperones. Several ligands which can activate or inhibit AHR have been described already, among them artificial or naturally occurring ones. The first ligands to be discovered were synthetic and members of the halogenated aromatic hydrocarbons (polychlorinated dibenzodioxins, such as 2,3,7,8-tetrachlorodibenzo-p-dioxin (TCDD), dibenzofurans and biphenyls) and polycyclic aromatic hydrocarbons (3-methylcholanthrene, benzo(a) pyrene, benzanthracenes and benzo flavones). Naturally occurring compounds that have been identified as ligands of AHR include derivatives of tryptophan such as kynurenin, indigo and indirubin, tetrapyroles such as bilirubin, arachidonic acid metabolites such as lipoxin A4 and prostaglandin G, modified low-density lipoprotein, several dietary carotinoids, and 7-ketocholesterol. Upon ligand binding, the chaperones dissociate resulting in AHR translocating into the nucleus and dimerizing with ARNT (AHR nuclear translocator). The complex of AHR and ARNT influences gene transcription.

The AHR polypeptide contains several domains critical for function and is classified as a member of the basic helix-loop-helix/Per-Arnt-Sim (bHLH/PAS) family of transcription factors. Its bHLH motif is located in the N-terminal of the protein. The members of the bHLH superfamily have two functionally distinctive and highly conserved domains. The first is the basic-region which is involved in the binding of the transcription factor to DNA. The second is the helix-loop-helix (HLH) region that facilitates protein-protein interactions. AHR further comprises two PAS domains, PAS-A and PAS-B, which are stretches of 200-350 amino acids that exhibit a high sequence homology to the protein domains which were found in the *Drosophila* genes period (Per) and single-minded (Sim). Moreover, similar domains are present in ARNT. The PAS domains support specific secondary interactions with other PAS domain containing proteins, as is the case with and ARNT, so that heterozygous and homozygous protein complexes can form. The ligand binding site of AHR is contained within the PAS-B domain and contains several conserved residues critical for ligand binding. In particular, the amino acids Tyr310, Phe324, His326 and/or Arg352 appear to be involved in ligand binding. Finally, a Q-rich domain is located in the C-terminal region of the protein and is involved in co-activator recruitment and transactivation.

Preferably, the AHR polypeptide is human AHR and, more preferably, human AHR encoded by a polynucleotide as shown under Genbank accession number: NM 001621.4 (GI: 229577137) or has an amino acid sequence as shown under this accession number. Moreover, in accordance with the present invention, variants of the AHR polypeptide referred to before are envisaged. Variants of the aforementioned polynucleotides comprising one or more nucleotide substitutions, deletions and/or additions and, preferably, result in an encoded amino acid having one or more amino acid substitutions, deletions and/or additions, i.e. a polypeptide variant according to the invention. A variant polynucleotide shall, preferably, comprise a nucleic acid sequence being at least 40%, at least 50%, at least 60%, at least 70%, at least 75%, at least 80%, at least 85%, at least 90%, at least 95%, at least 98% or at least 99% identical to the specific nucleic acid sequences referred to above. Moreover, a variant polynucleotide may have, preferably, a nucleic acid sequence which encodes an amino acid sequence being at least 40%, at least 50%, at least 60%, at least 70%, at least 75%, at least 80%, at least 85%, at least 90%, at least 95%, at least 98% or at least 99% identical to the amino acid sequences referred to above. The term "identical" as used herein refers to sequence identity characterized by determining the number of identical amino acids between two nucleic acid sequences or amino acid sequences wherein the sequences are aligned so that the highest order match is obtained. It can be calculated using published techniques or methods codified in computer programs such as, for example, BLASTP, BLASTN or FASTA (Altschul 1990, J Mol Biol 215, 403). The percent identity values are, in one aspect, calculated over the entire amino acid sequence or over at least 50% of the nucleotides of the longer sequence. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (Higgins 1989, CABIOS 5, 151) or the programs Gap and BestFit (Needleman 1970, J Mol Biol 48; 443; Smith 1981, Adv Appl Math 2, 482), which are part of the GCG software packet (Genetics Computer Group 1991, 575 Science Drive, Madison, Wis., USA 53711), may be used. The sequence identity values recited above in percent (%) are to be determined, in another aspect of the invention, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments. It will be understood that the aforementioned variants shall still exhibit essentially the same biological activities specified for AHR above.

A compound which directly inhibits the AHR activity is, preferably, a compound which is capable of interacting physically with the AHR polypeptide and, thereby, inhibiting its activity. Such an inhibition may occur if the compound binds to an interaction domain of the AHR or its ligand binding domain and thereby inhibits the biological function of the AHR as specified elsewhere herein. Preferably, the inhibitor blocks the ligand binding domain for kynurenin, i.e. interacts with the ligand binding domain of the PAS-B domain or the ligand binding domain formed by Tyr310, Phe324, His326 and Arg352 (amino acid positions corresponding to human AHR). Alternatively, the compound may elicit an allosteric effect on the AHR polypeptide resulting in an inhibition of the biological function as well. An indirect inhibition can be elicited by a compound which reduces or prevents the transcription and/or translation of AHR polypetides and, thus, the amount of available AHR polypeptides in a cell. The AHR inhibitor shall at least reduce the AHR activity to a statistically significant extent. Of course, preferably, the inhibitor will reduce the AHR activity below the detectable limits. Qualitative and/or quantitative inhibition of AHR activity can be measured by assays well known in the art and, preferably, by those disclosed in the accompanying Examples, below. The activity of AHR can be detected by determining induction of the gene expression of its endogenous target gene CYP1A1 by an ethoxyresorufin-O-deethylase (EROD) assay.

Alternatively, activity of AHR can be detected by using a reporter gene assay wherein the expression of the reporter gene is controlled by a dioxin-responsive element (DRE) dependent promoter. Particular preferred assays for determining AHR activity are disclosed in the accompanying Examples in detail.

Preferably, an AHR inhibitor is a small molecule compound.

A "small molecule compound" in the sense of the invention is an organic molecule having a molecular weight of less than 10 kDa, less than 5 kDa, less than 2 kDa, less than 1 kDa or less than 500 Da. Preferably, the small molecule is not a polymer. Preferably, a small molecule as referred to in accordance with the present invention is cell-permeable and can diffuse into the cytoplasm in order to bind to the AHR polypeptide. Small molecules as referred to herein can be artificially synthesized and can be comprised in chemical libraries to be screened for potential AHR inhibitors. Alternatively, the small molecules can be obtained from natural sources such as tissues, cells or whole organisms by way of extraction. Suitable sources are, in particular, plants, plant tissue or microorganisms. However, other sources for small molecule inhibitors for AHR can be envisaged as well. For example, 7-ketocholesterol is apparently a competitive inhibitor of AHR in humans (Savouret 2001, J. Biol. Chem. 276 (5): 3054-9).

In a preferred embodiment of the method of the invention, said small molecule compound is a plant compound or derivative thereof.

A "plant compound or derivative thereof" as used herein is a small molecule obtainable by way of extraction from a plant, plant tissue or plant cell. Usually, small molecule plant compounds are metabolites such as primary or, particularly preferred, secondary plant metabolites. In a more preferred embodiment of the method of the invention, said plant compound or derivative thereof is a flavone or a derivative thereof. Most preferably, said flavone or derivative hereof is 3,4-dimethoxyflavone, 3'-methoxy-4'-nitroflavone, 4',5,7-Trihydroxyflavone (apigenin) or 1-Methyl-N-[2-methyl-4-[2-(2-methylphenyl)diazenyl]phenyl-1H-pyrazole-5-carboxamide. In another more preferred embodiment of the method of the invention, said plant compound or derivative thereof is resveratrol (trans-3,5,4'-Trihydroxystilbene) or a derivative thereof, epigallocatechin or epigallocatechingallate.

In another preferred embodiment of the method of the invention, wherein said small molecule compound is a compound characterized by the following general formula (I):

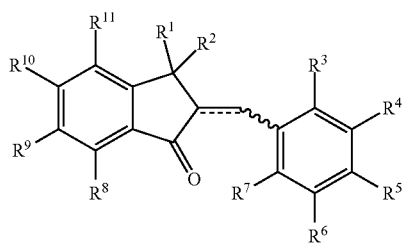

wherein
(i) $R^1$ and $R^2$ independently of each other are hydrogen or a $C_1$ to $C_{12}$ alkyl,
(ii) $R^3$ to $R^{11}$ independently from each other are hydrogen, a $C_1$ to $C_{12}$ alkyl, hydroxyl or a $C_1$ to $C_{12}$ alkoxy, and (iii) the broken line represents either a double bond or two hydrogens.

In particular, more preferred is a compound having any of the following formulas (II) to (V):

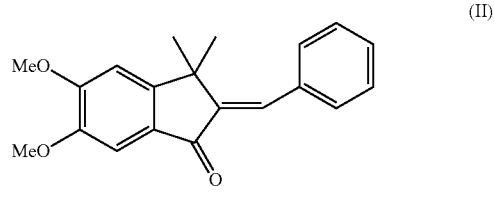
(II)

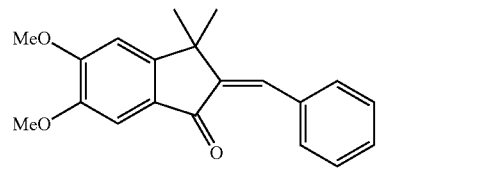
(III)

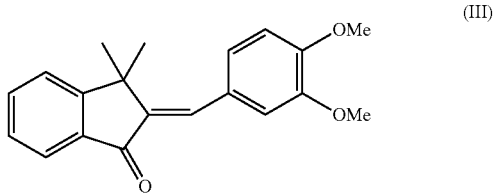
(IV)

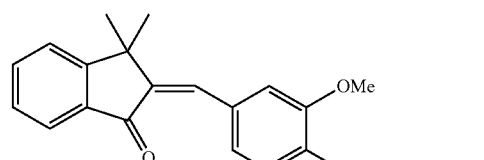
(V)

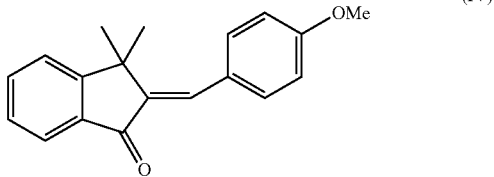

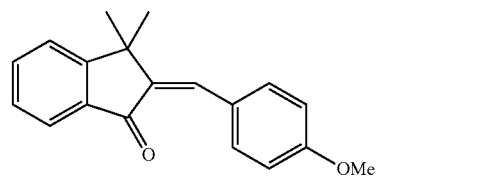

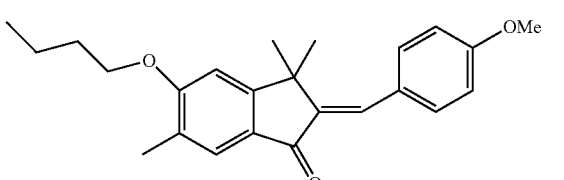

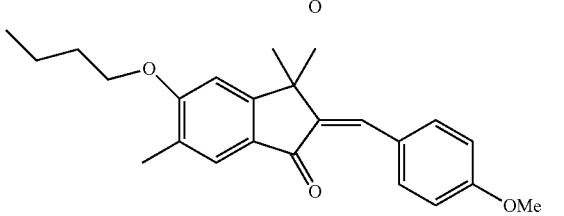

Further more preferred compounds and methods for the manufacture thereof are disclosed in WO2007/128723, the respective disclosure content of which is herewith incorporated by reference.

In another preferred embodiment of the method of the invention, said AHR inhibitor is an antibody which specifically binds to and inhibits the AHR protein.

The term "antibody" as used in this context refers to all kinds of antibodies which specifically bind to the AHR polypeptide and which inhibit the AHR activity as specified elsewhere herein. Preferably, such an inhibitory antibody of the invention shall specifically bind to an epitope within the AHR polypeptide which is located in the ligand binding domain. Alternatively, an epitope binding of which by the antibody shall inhibit AHR activity may be located in the DNA binding domain of AHR or in domains responsible for interaction with the ARNT polypeptide. Suitable domains are discussed elsewhere herein in detail. Preferably, the antibody of the present invention is a monoclonal antibody, a polyclonal antibody, a single chain antibody, a chimeric antibody or any fragment or derivative of such antibodies. Such fragments and derivatives comprised by the term antibody as used herein encompass a bispecific antibody, a synthetic antibody, an Fab, F(ab)$_2$ Fv or scFv fragment, or a chemically modified derivative of any of these antibodies. Specific binding as used in the context of the antibody of the present invention means that the antibody does not cross react with other polypeptides. Specific binding can be tested by various well known techniques.

Antibodies or fragments thereof, in general, can be obtained by using methods which are described, e.g., in Harlow and Lane "Antibodies, A Laboratory Manual", CSH Press, Cold Spring Harbor, 1988. Monoclonal antibodies can be prepared by the techniques which comprise the fusion of mouse myeloma cells to spleen cells derived from immunized mammals and, preferably, immunized mice (Köhler 1975, Nature 256, 495, and Galfré 1981, Meth. Enzymol. 73, 3). Preferably, an immunogenic peptide having the epitope referred to above is applied to a mammal. Depending on the host species, various adjuvants can be used to increase the immunological response. Such adjuvants encompass, preferably, Freund's adjuvant, mineral gels, e.g., aluminum hydroxide, and surface active substances, e.g., lysolecithin, pluronic polyols, polyanions, peptides, oil emulsions, keyhole limpet hemocyanin, and dinitrophenol.

In another preferred embodiment of the method of the invention, said AHR inhibitor is the AHR repressor protein or an inactive AHR nuclear translocator (ARNT).

The term "AHR repressor (AHRR)" as used herein refers to a putative tumor supressor gene that negatively regulates the activity of AHR and the AHR/ARNT complex. Preferably, a polynucleotide encoding the AHRR polypeptide as well as an amino acid sequence for the AHRR polypeptide itself as referred to herein are shown in Genbank accession number: BC151852 (GI: 156229770). Moreover, an AHRR polypeptide in accordance with the present invention may be a variant of the aforementioned specific polynucleotides or polypeptides. Variants of the aforementioned polynucleotides comprising one or more nucleotide substitutions, deletions and/or additions and, preferably, result in an encoded amino acid having one or more amino acid substitutions, deletions and/or additions, i.e. a polypeptide variant according to the invention. A variant polynucleotide shall, preferably, comprise a nucleic acid sequence being at least 40%, at least 50%, at least 60%, at least 70%, at least 75%, at least 80%, at least 85%, at least 90%, at least 95%, at least 98% or at least 99% identical to the specific nucleic acid sequences referred to above. Moreover, a variant polynucleotide may have, preferably, a nucleic acid sequence which encodes an amino acid sequence being at least 40%, at least 50%, at least 60%, at least 70%, at least 75%, at least 80%, at least 85%, at least 90%, at least 95%, at least 98% or at least 99% identical to the amino acid sequences referred to above. How the sequence identity between two given sequences can be calculated is disclosed elsewhere herein in detail.

As discussed before, inactive versions of the ARNT polypeptide can be designed by the skilled person without further ado based on the aforementioned specific polynucleotide or amino acid sequences or the variants thereof. Moreover, these inactive ARNT polypeptides or polynucleotides encoding them can be introduced into the cancer cells to be treated by methods well known in the art. In particular, gene transfer via viral expression systems is envisaged in accordance with the present invention as a delivery system for polynucleotides encoding inactive ARNT. Suitable techniques are well known in the art (see above).

The term "AHR Nuclear Translocator (ARNT)" as used herein refers to a binding protein for the AHR transcription factor. Details are found elsewhere in this specification already. The ARNT polypeptide referred to herein as an inhibitor of AHR is a polypeptide which is still capable of interacting with AHR but which prevents nuclear translocation or which directs the AHR/ARNT complex to the protein degradation machinery of the cell. How such modified inhibitory ARNT polypeptides can be designed is well known to the skilled person. Preferably, a polynucleotide encoding the (unmodified) ARNT polypeptide as referred to herein is shown in Genbank accession number: NM_001197325.1 (GI: 309747070). Preferably, said polynucleotide encodes a polypeptide having an amino acid sequence as shown in Genbank accession number: (protein) NP_001184254.1 (GI: 309747071). Moreover, an ARNT polypeptide in accordance with the present invention may be a variant of the aforementioned specific ARNT polynucleotides or polypeptides. Variants of the aforementioned polynucleotides comprising one or more nucleotide substitutions, deletions and/or additions and, preferably, result in an encoded amino acid having one or more amino acid substitutions, deletions and/or additions, i.e. a polypeptide variant according to the invention. A variant polynucleotide shall, preferably, comprise a nucleic acid sequence being at least 40%, at least 50%, at least 60%, at least 70%, at least 75%, at least 80%, at least 85%, at least 90%, at least 95%, at least 98% or at least 99% identical to the specific nucleic acid sequences referred to above. Moreover, a variant polynucleotide may have, preferably, a nucleic acid sequence which encodes an amino acid sequence being at least 40%, at least 50%, at least 60%, at least 70%, at least 75%, at least 80%, at least 85%, at least 90%, at least 95%, at least 98% or at least 99% identical to the amino acid sequences referred to above. How the sequence identity between two given sequences can be calculated is disclosed elsewhere herein in detail.

AHRR polypeptides or polynucleotides encoding them can be introduced into the cancer cells to be treated by methods well known in the art. In particular, gene transfer via viral expression systems is envisaged in accordance with the present invention as a delivery system for polynucleotides encoding inactive ARNT. Suitable techniques are well known in the art and described, e.g. in Gardlik 2005, Med Sci Monit. 11 (4): RA110-21; Salmons 1993, Hum Gene Ther. 4 (2): 129-41.

In another preferred embodiment of the method of the invention, wherein said AHR inhibitor is a nucleic acid inhibitor.

A "nucleic acid inhibitor" as referred to herein is a nucleic acid molecule such as an aptamer which inhibits either the activity of the AHR polypeptide by binding to the polypeptide in a similar manner as described for the antibodies above or to a nucleic acid molecule which due to being complementary to the polynucleotide encoding the AHR polypeptide binds to the said polynucleotide and inhibits transcription or translation thereof. For example, an inhibitory nucleic acid may act as a triple-helix forming oligonucleotide by interfering with proper transcription of the AHR gene. Moreover, an inhibitory nucleic acid may be a ribozyme which specifically binds and degrades the AHR transcripts. Alternatively, it may be an antisense, siRNA or micro RNA capable of binding to the transcript and degrading it or at least inhibiting efficient translation thereof. The latter type of inhibitory nucleic acids is characterized in that they usually comprise a nucleic sequence which is complementary to a sequence in the AHR transcripts. Such a complementary sequence shall be of sufficient length and shall comprise a sufficient number of matching nucleotides as to allow for specific hybridization with the transcript in the cell. Such nucleic acid inhibitors can be expressed in a cancer cell upon delivery by a gene transfer system as referred to elsewhere herein. The inhibitory nucleic acids can be expressed, preferably, under an expression control sequence. Thus, the mediation of RNAi to inhibit expression of the target gene can be modulated by an expression control sequence which can be regulated by a exogenous stimulus, such as the tet operator whose activity can be regulated by tetracycline or heat inducible promoters or under the control of a tumor-specific or tissue-specific promoter. However, the nucleic acid inhibitors can also be delivered by liposome-based delivery systems.

Thus, in another more preferred embodiment of the method of the invention, said nucleic acid inhibitor is selected from the group consisting of a ribozyme, an antisense molecule, an inhibitory oligonucleotide, an aptamer, a micro RNA, and an siRNA.

A "ribozyme" in accordance with the present invention is a RNA molecule comprising a sequence complementary to the AHR transcript. Moreover, the ribozyme comprises a nucleic acid sequence which is capable of eliciting the hydrolysis of the phosphodiester bonds within the AHR transcript. Ribozymes as referred to in accordance with the present invention can be so-called hammerhead ribozymes, hairpin ribozymes or VS ribozymes. The ribozyme technology is well known in the art and a suitable ribozyme can be designed and applied by the skilled artisan without further ado; see, e.g., Khan 2006, Clin. Chim. Acta 367 (1-2): 20-27; Kalota 2004, Cancer Biology & Therapy 3:1 4-12.

An "antisense molecule" as used herein refers to a therapeutic antisense RNA being complememtary to the AHR transcript or to a morpholino oligonucleotide capable of binding the AHR transcript. The antisense technology including the application of morpholino oligonucleotides is well known in the art; see, e.g., Kalota 2004, Cancer Biology & Therapy 3:1 4-12; Morcos 2007, Biochem Biophys Res Commun 358 (2): 521-7.

Inhibitory oligonucleotides as used herein, preferably, relate to small double stranded DNA molecules which are either capable of binding to specific regions of a target genomic DNA whereby gene silencing is achieved (so-called triple helix forming oligonucleotides) or to oligonucleotides which act as decoys to sequester transcription factor specifically required for the transcription of a target gene These techniques have also been successfully used in vivo and also to some extend resulted already in therapeutics. (see also Kalota 2004, Cancer Biology & Therapy 3:1 4-12.).

The term "aptamer" as used herein refers to nucleic acid aptamers that specifically bind to the AHR polypeptide. A pool of aptamers can be generated by using, e.g., the Systematic Evolution of Ligands by Exponential Enrichment (SELEX) technology. The selection step can be made for those aptamers which apecifically bind to the AHR polypeptide. Among the specifically binding aptamers, those which either block ligand binding or those which block interaction domains and are, thus, suitable inhibitors in the sense of the present invention can be identified. The technology for generating aptamers is well established in the art; see, e.g., Tuerk 1990, Science. August 3; 249(4968):505-510; or Ellington 1990, Nature. August 30; 346(6287):818-822.

A "microRNA" in the sense of the invention refers to a single stranded RNA molecule which is at least partially complementary to a nucleic acid sequence comprised by the AHR transcript. MicroRNAs have usually a length of about 19 to 26 nucleotides. MicroRNAs are synthesized as a precursor, the so-called pri-microRNA, which comprises a harpin structure and two complementary self-complementary regions forming the stem of the hairpin. One of the self-complementary nucleic acid sequences is the microRNA. The pri-microRNA has a length of about 70 nucleotides and is processed within the target cell into the mature microRNA. The mature microRNA is capable of downregulating gene expression by either affecting translation or stability of the mRNA to be transcribed upon hybridization thereto. How to design a microRNA and its pri-microRNA precursor is well known to the skilled person. In particular, the self-complementary regions of an endogenous pri-microRNA molecule are replaced by a pair of self-complementary regions comprising one self-complementary region being at least partially complementary to the AHR transcript. The microRNA technology is descried in, e.g., Bartel 2009, Cell 136 (2): 215-33, Trang 2008, Oncogene 27 Suppl 2: S52-7 or Li 2009, The AAPS journal 11 (4): 747-57.

A "short hairpin RNA (shRNA)" as referred to in accordance with the present invention has a similar structure as described for pri-microRNAs above. However, the shRNA is, usually, shorter in length. More preferably, an shRNA as referred to in accordance with the present invention as an AHR inhibitor is a nucleic acid molecule comprising or essentially consisting of the nucleic acid sequence as shown in any one of SEQ ID NOs: 1 to 4. The design and application of shRNAs is well known in the art and described, e.g., in McIntyre 2006, BMC Biotechnol. 6: 1 or Cao 2005, J Appl Genet. 46 (2): 217-25.

The term "small interfering RNA (siRNA)" refers to a nucleic acid molecule which is a double stranded RNA agent that is complementary and able to base-pair with a portion of an AHR transcript. siRNA acts to specifically guide enzymes in the host cell to cleave the target RNA. By virtue of the specificity of the siRNA sequence and its homology to the RNA target, siRNA is able to cause cleavage of the target RNA strand, thereby inactivating the target RNA molecule. Preferably, the siRNA which is sufficient to mediate RNAi comprises a nucleic acid sequence comprising an inverted repeat fragment of the target gene and the coding region of the gene of interest (or portion thereof). The complementary regions of the siRNA allow sufficient hybridization of the siRNA to the target RNA and thus mediate RNAi. In mammalian cells, siRNAs are approximately 19-25 nucleotides in length. The siRNA sequence needs to be of sufficient length to bring the siRNA and target RNA together through complementary base-pairing interactions. The length of the siRNA is preferably greater than or equal to ten nucleotides and of sufficient length to stably interact with the target RNA; specifically 15-30 nucleotides; more specifically any integer between 15 and 30 nucleotides, most preferably 15, 16, 17, 18, 19, 20, 21, 22, 23, 24, 25, 26, 27, 28, 29, and 30. By sufficient length it is meant an oligonucleotide of greater than or equal to 15 nucleotides that is of a length great enough to provide the intended function under the expected condition. By stable interaction it is meant interaction of the small interfering RNA with target nucleic acid (e.g., by forming hydrogen bonds with complementary nucleotides in the target under physiological conditions). Generally, such a degree of complementary is 100% between the siRNA and the RNA target, but can be less if desired, preferably 91%, 92%, 93%, 94%, 95%, 96%, 97%, 98%, or 99%. For example, 19 bases out of 21 bases may be base-paired. In some instances, where selection between various allelic variants is desired, 100% complementary to the target gene is required in order to effectively discern the target sequence from the other allelic sequence. Methods relating to the use of RNAi to silence genes in organisms, including *C. elegans, Drosophila*, plants, and mammals, are known in the art (see, e.g., Fire 1998, Nature 391:806-811; Fire 1999, Trends Genet. 15, 358-363; WO2001/29058; WO2009/932619).

Finally, contemplated, in general, by the invention is a AHR inhibitor, preferably as defined herein above, for use in treating and/or preventing cancer associated with increased tryptophan-2,3-dioxygenase (TDO) activity.

Cancer-associated immunosuppression by Trp degradation has to date been attributed pivotally to the enzymatic activity of IDO in cancer cells and tumor-draining lymph nodes. Thus, IDO inhibition is currently being evaluated as a therapeutic strategy to treat cancer in clinical trials despite some off-target effects on human cancer cells. In the studies underlying this invention it was shown that TDO is strongly expressed in cancer and equally capable of producing immunosuppressive Kyn. In IDOnegative glioma cells, TDO appears to be the sole determinant of constitutive Trp degradation, indicating that TDO represents a novel therapeutic target in glioma therapy. In fact, an orally available TDO inhibitor has recently been developed. Inhibition of TDO may not only restore antitumor immune responses but also act on the tumor cell intrinsic malignant phenotype as we delineated the importance of constitutive Trp degradation to sustain the malignant phenotype of cancer by acting on the tumor cells themselves. Emerging evidence points towards a tumor-promoting role of the AHR. AHR activation promotes clonogenicity and invasiveness of cancer cells. Transgenic mice with a constitutively active AHR spontaneously develop tumors and the repressor of the AHR (AHRR) is a tumor suppressor gene in multiple human cancers. The aberrant phenotype of Ahr-deficient mice points to the existence of endogenous AHR ligands. While different endogenously produced metabolites such as arachidonic acid metabolites, bilirubin, cAMP, tryptamine and 6-formylindolo[3,2-b]carbazole (FICZ) have been shown to be agonists of the AHR, their functionality has not been convincingly demonstrated in a pathophysiological context such as cancer or immune activation. The search for endogenous ligands of the AHR therefore is ongoing.

In accordance with the present invention, these two important pathways contributing to cancer progression by showing that Trp catabolism leads to AHR activation and provide evidence of a pathophysiological human condition that is associated with the production of sufficient amounts of a functionally relevant endogenous AHR ligand. The results of the studies underlying the present invention reveal a differential response of primary immune cells and transformed cancer cells to AHR-mediated signals, which is in line with various toxicological studies using the classical exogenous AHR ligands, TCDD and 3-MC. Exposure to these xenobiotics leads to profound suppression of cellular and humoral immune responses, while also promoting carcinogenesis and inducing tumor growth. These cell-specific differences in AHR effects are likely to depend on the expression of factors differentially regulating AHR signal transduction such as the AHRR as well as cell-specific transcription factor crosstalk shaping the response to AHR activation. It is likely that Kyn-mediated activation of the AHR is not only relevant in the setting of cancer. For instance, activation of the mouse and human AHR by agonistic ligands induces regulatory T cells. Interestingly, Ahr-deficient mice suffer from exacerbated CNS autoimmunity in the absence of an exogenous ligand, while Trp catabolites suppress CNS autoimmunity suggesting that activation of Trp catabolism represents an endogenous feedback loop to restrict inflammation via the AHR. In fact, exogenous Kyn is involved in the regulation of immune cells in mice via the AHR. Kyn concentrations sufficient to activate the AHR are also generated by IDO in response to inflammatory stimuli. In a broader context, a significant number of malignancies arise from areas of mostly chronic infection and inflammation, where Trp catabolism in the tumor microenvironment is activated and sustains local immune suppression. Activation of the AHR by Kyn generated in response to inflammatory stimuli may thus constitute a previously unrecognized pathway connecting inflammation and carcinogenesis.

All references cited in this specification are herewith incorporated by reference with respect to their entire disclosure content and the disclosure content specifically mentioned in this specification.

EXAMPLES

The invention will now be described by the following examples which, however, must not be construed as limiting the scope of the invention.

Example 1

Materials and General Methods

Cells and Reagents

The origin and culture conditions of cell lines are detailed in the Supplementary Methods. All glioma initiating cells (GIC) were established from freshly resected tumors and used during the first passages. All cells were routinely tested for bacterial contamination. Trp-free RPMI 1640 (Promocell) and dialysed FBS (Invitrogen) were used to cultivate cells under Trp-free conditions. L-Trp and L-Kyn were from Sigma-Aldrich. Interferon-γ (IFN-γ) was from Immunotools (Friesoythe, Germany). TCDD and 3-methylcholanthrene (3-MC) were from Sigma-Aldrich and 3,4-dimethoxyflavone (3,4-DMF) was from Alfa Aesar (Karlsruhe, Germany). The TDO inhibitor ((E)-6-fluoro-3-[2-(3-pyridyl) vinyl]-1H-indole) 680C91 was synthesised by condensation of 6-Fluoroindole-3-carboxaldehyde with pyridine-3-acetic acid in the presence of piperidine.

Mice

C57BL/6N and CD-1 nu/nu mice were purchased from Charles River (Sulzfeld, Germany). Ahr-deficient mice (B6.129-AHRtmlBra/J) were kindly provided by Charlotte Esser (Dusseldorf, Germany). C57BL/6N that were age-matched with the Ahr-deficient mice were from Harlan Laboratories (Rossdorf, Germany).

TDO Expression Analysis

TDO expression was analysed by immunohistochemistry in human tumors. Its relevance for Trp degradation was determined using genetic knockdown or overexpression of TDO. Trp and Kyn were measured in cell culture supernatants, human sera and xenograft tissue by HPLC. Mixed leukocyte reactions, chromium release, ELISpot and staining of immune cells in tumor tissues were used to assess the immune effects of TDO activity. Cell cycle analysis, matrigel and spheroid invasion assays, scratch assays, sphere formation assays and clonogenicity assays were employed to analyse the autocrine effects of TDO activity. All animal procedures followed the institutional laboratory animal research guidelines and were approved by the governmental authorities. Orthotopic implantation of human glioma cells with and without stable knockdown of TDO into CD1nu/nu mice, s.c. injection of these cells into NK-depleted or wildtype CD1nu/nu mice and s.c. injection of murine Tdo-proficient and Tdo-deficient GL261 cells into syngeneic C57BL/6N mice were performed to analyse the autocrine and paracrine effects of TDO activity in vivo. Microarray analysis of Kyn-treated human glioma cells was performed to identify signalling pathways activated by Kyn. Analysis of AHR translocation, DRE-luciferase assays and radioligand binding assays confirmed activation of the AHR by Kyn. Pharmacological inhibition and stable knockdown of the AHR (in vitro and in vivo) proved that the effects of Kyn are AHR-dependent. Injection of doproficient and Tdo-deficient tumor cells into Ahr+/+ and Ahr-/- mice was used to address the contribution of host effects to TDO-mediated cancer promotion. Finally, stainings, mircoarray data and clinical data of human tumor tissues were used to analyse whether TDO activates the AHR in human cancers and how this affects survival.

Analysis of Trp and Kyn Concentrations by High Performance Liquid Chromatography (HPLC)

HPLC analysis was performed using a Beckman HPLC with photodiode array (PDA) detection and Lichrosorb RP-18 column (250 mm×4 mm ID, 5 µm, Merck, Darmstadt, Germany). Kyn and Trp concentrations were measured in the medium of 3×105 cells. Human serum was obtained from 24 glioblastoma patients (10 females, 14 males, median age 54.5 years) and 24 age- and sex-matched healthy controls (10 females, 14 males, median age 53.5 years) after informed consent and analysed for Trp and Kyn concentrations. For measurement of Kyn concentrations in U87 xenografts, the U87 tumors were excised, weighed, immediately frozen in liquid nitrogen and processed.

Quantitative (q)RT-PCR

Total RNA was isolated with the Qiagen RNeasy kit and cDNA was synthesised with the Applied Biosystems reverse transcription kit (Foster City, Calif., USA). QRT-PCR was preformed in an ABI 7000 thermal cycler with SYBR Green PCR Mastermix (both Applied Biosystems). All primers were separated by at least one intron on the genomic DNA to exclude amplification of genomic DNA. PCR reactions were checked by including no-RT controls, by omission of templates and by both melting curve and gel analysis. Standard curves were generated for each gene. Relative quantification of gene expression was determined by comparison of threshold values. All results were normalised to GAPDH.

siRNA Experiments

To knockdown IDO1 (INDO), IDO2 and TDO (TDO2) SMART-pool siRNA by Dharmacon RNA Technologies (Lafayette, Colo., USA) was used. The target sequences were as follows:

```
Human INDO (Genbank accession number
NM_002164):
                                        (SEQ ID NO: 5)
5'-UCACCAAAUCCACGAUCAUUU-3';

(SEQ ID NO: 6)
5'-UUUCAGUGUUCUUCGCAUAUU-3';

(SEQ ID NO: 7)
5'-GUAUGAAGGGUUCU GGGAAUU -3';

(SEQ ID NO: 8)
5'-GAACGGGACACUUUGCUAAUU-3'

Human IDO2 (Genbank accession number
NM_194294):
                                        (SEQ ID NO: 9)
5'-CAAACUUCCUCAAUUGAUU-3';

(SEQ ID NO: 10)
5'-UUGGAAAGCUAUCACAUAU-3';

(SEQ ID NO: 11)
5'-GAGUAUGGCUUUCUUCUUC-3';

(SEQ ID NO: 12)
5'-GCACCCAGUUGAAGUUUAA-3'

Human TDO2 (Genbank accession number
NM_005651):
                                        (SEQ ID NO: 13)
5'-UCAUAAGGAUUCAGGCUAA-3';

(SEQ ID NO: 14)
5'-AGUGAUAGGUACAAGGUAU-3';

(SEQ ID NO: 15)
5'-GGAUUUAACUUCUGGGGAA-3';

(SEQ ID NO: 16)
5'-GCGAAGAAGACAAAUCACA-3'

TDOA shRNA sense:
                                        (SEQ ID NO: 17)
5'-GGAAAGAACTCCAGGTTTATTCAAGAGATAAACCTGGAGT

TCTTTCC-3'

TDOA shRNA antisense:
                                        (SEQ ID NO: 18)
5'-CCTTTCTTGAGGTCCAAATAAGTTCTCTATTTGGACCTCA

AGAAAGG-3'

TDOB shRNA sense:
                                        (SEQ ID NO: 19)
5'-TCATAAGGATTCAGGCTAATTCAAGAGATTAGCCTGAATC

CTTATGA-3'

TDOB shRNA antisense:
                                        (SEQ ID NO: 20)
5'-AGTATTCCTAAGTCCGATTAAGTTCTCTAATCGGACTTAG

GAATACT-3'
```

ON-TARGETplus siCONTROL Non-targeting Pool (D-001810-10-05, Dharmacon) and a transfection without siRNA were used as negative controls. Cells were transfected using the lipofectamine RNAiMAX from Invitrogen. Knockdown efficiency was analysed by qRT-PCR.

Stable Knockdown Cells

U87 human glioma cells were transfected with pSUPER-.puro plasmid (OligoEngine, Seattle, Wash., USA) expressing sh-TDO or scrambled control using FUGENE HD transfection reagent (Roche, Mannheim, Germany). 72 h after transfection medium was exchanged to DMEM containing 5 µg/ml puromycin (AppliChem GmbH). If not indicated otherwise sh-TDOA was used. For knockdown of the AHR in LN308 glioma cells the pSingle-tTS-shRNA vector was purchased from Clontech (CA, USA) Annealed ds oligonucleotides encoding the desired shRNA sequences with XhoI/HindIII overhangs were cloned into the vector using the XhoI/HindIII cloning sites. Short hairpin sequences for control/AHR or TDO shRNA silencing including the XhoI/HindIII overhangs were as follows:

```
scrambled shRNA antisense oligo:
                                (SEQ ID No: 21)
5'-AGCTTGGATCCAAAAAAGTACTTCCACCTCAGTTGGC

TCTCTTGAAGCCAACTGAGGTGGAAGTACC-3', scrambled shRNA sense oligo:
                                (SEQ ID NO: 22)
5'-TCGAGGTACTTCCACCTCAGTTGGCTTCAAGAGAGCCA

ACTGAGGTGGAAGTACTTTTTTGGATCCA-3',

AHR shRNA antisense oligo:
                                (SEQ ID NO: 1)
5'-AGCTTGGATCCAAAAAAGCGTTTACCTTCAAACTTTATC

TCTTGAATAAAGTTTGAAGGTAAACGCC-3',

AHR shRNA sense oligo:
                                (SEQ ID NO: 2)
5'-TCGAGGCGTTTACCTTCAAACTTTATTCAAGAGATAAA

GTTTGAAGGTAAACGCTTTTTTGGATCCA-3',

AHR shRNA antisense oligo (Dharmacon siRNA
#6 of Smart pool of AHRAHR siRNA):
                                (SEQ ID NO: 3)
5'-AGCTTGGATCCAAAAAAGGAACTCAAGCTGTATGGTATCT

CTTGAATACCATACAGCTTGAGTTCCC-3',

AHR shRNA sense oligo (Dharmacon):
                                (SEQ ID NO: 4)
5'-TCGAGGGAACTCAAGCTGTATGGTATTCAAGAGATACCA

TACAGCTTGAGTTCCTTTTTTGGATCCA-3'.
```

The recombinant vector was transfected into LN-308 and LN-18 glioma cells and clonal transformants were selected with 1 mg/ml neomycin (Sigma-Aldrich). The knockdown was induced using 2 µg/ml doxicyclin (Sigma-Aldrich), cells were analysed 72 h after induction. If not indicated otherwise sh-AHR1 was used.

Stable Overexpression

GL261 cells were transfected with either pcDNA3.1 (−) (Invitrogen), expressing Tdo cDNA (NM_019911) or empty vector using FUGENE HD reagent (Roche). Clonal transformants were selected using 1 mg/ml neomycin (Sigma-Aldrich).

Tissue Specimens and Immunohistochemistry

Sections cut to 3 µm were incubated and processed with the respective antibody using a Ventana BenchMark XT® immunostainer (Ventana). For quantitative analysis of TDO staining, the percentage of stained tumor cells and intensity of staining were evaluated in representative magnification fields (200×) on tissue sections using optical microscopy (Olympus BX51).

Immunofluorescent Stainings

For immunofluorescence, sections of gliomas with low TDO expression and gliomas with high TDO expression were incubated with rabbit anti-TIPARP (1:50) and mouse anti-LCA (1:50) antibodies overnight at 4° C. after 30 min of heat-mediated antigen retrieval in Ventana cell conditioner 1. Then, donkey anti-rabbit AlexaFluor 568 (1:500, Invitrogen) and donkey anti-mouse DyLight 488 (1:100, Jackson ImmunoResearch, West Grove, Pa., USA) secondary antibodies were applied for 5 h. Micrographs were taken at a Olympus BX-50 microscope (Olympus GmbH, Hamburg, Germany) using the Zeiss Axiocam MRm (Zeiss, Jena, Germany).

Mixed Leukocyte Reaction (MLR)

Glioma cells were seeded in 96-well plates in RPMI 1640 containing 10% FBS, 100 U/ml penicillin and 100 µg/ml streptomycin. 24 h after seeding 2×105 irradiated (30 Gy) PBMC as stimulators and 2×105 PBMC from unrelated donors as responders were added. Six-day MLR were performed and cultures were pulsed with [3H]-methylthymidine (PerkinElmer, Waltham, Mass., USA) for the last 18 h. Cells were harvested, and radionuclide uptake was measured by scintillation counting. Experiments were repeated with six unrelated PBMC donors.

Reporter Assay

Dual luciferase/renilla assays were performed as detailed in the Supplementary Methods. For analysis of DRE-driven reporter gene activity in response to various Trp metabolites, the pGL3-promotor expression plasmid and the control plasmid pRL-SV40, expressing renilla luciferase were used (Promega, Heidelberg, Germany).

Invasion Assays

In matrigel assays cell invasion was evaluated by counting the number of cells that had migrated across the membrane in 5 independent microscopic high-power fields and expressed as percentage of invasiveness relative to control using a microgrid. In spheroid assays microscopic photographs of the area covered by each spheroid were taken at 0, 24, 48 and 72 h after implantation. For quantification, the mean area which was covered by invaded glioma cells at an indicated time point was measured in intervals of 24 h and compared with the area at 0 h with ImageJ.

Chromium Release Assay

Inhibition of immune cell cytotoxicity was assessed using the standardised 51 chromium release assay (Supplementary Methods). Specific lysis in percent was calculated as follows: [Experimental 51Cr Release−Minimum Release]/ [Maximum Release−Minimum Release]×100. This experiment was performed with at least 4 different PBMC donors.

Enzyme Linked Immuno Spot Technique Assay (ELISpot)

Dendritic cells (DC) were isolated from the bone marrow of healthy C57BL/6N mice and cultured in RPMI 1640 containing 20 ng/ml GM-CSF (Immunotools) for 5 days. Spleens from tumor-bearing mice were removed and mashed through a 40-µm cell strainer. Erythrocytes were lysed and T cells were isolated by MACS using the pan T cell isolation kit II (Miltenyi GmbH). 2×105 DC were seeded in an ELISpot plate (Millipore) that had been coated with anti-IFNγ antibody (Mabtech AB, Nacka Strand, Sweden) and pulsed with 10 µg GL261 lysate—generated in PBS by repeated freeze thaw cycles—for 4 h before addition of 1×105 T cells. After 36 h, IFNγ-producing T cells were detected with biotinylated anti-IFNγ antibody, streptavidin-ALP and BCIP/NBTPLUS (Mabtech) and quantified using an ImmunoSpot Analyzer (Cellular Technology Limited, Shaker Heights, Ohio, USA).

Detection of AHR Translocation

For detection of AHR translocation 7000 Tao BpRc1c cells with a GFP-tagged AHR per well were exposed to 50 µM Kyn or 50 µM Trp, fixed in 3.7% formaldehyde in PBS, permeabilised in 0.1% Triton X100, incubated with 1 µg/ml Hoechst 33342 (Invitrogen) and imaged on a BD Pathway™ Imager 855 in a non-confocal mode using a 20× U-Apo 340 objective (Olympus, NA 0.75). Further analysis of fluorescence intensity was performed using the Attovision software (BD Biosciences). In addition, the AHR protein content in the nuclear and the cytoplasmic fractions of LN-229 glioma cells was compared by immunoblotting.

Radioligand Binding Assay with 3H-Labelled Kyn

L-3H-Kyn with a specific activity of 11 Ci/mmol was obtained from Quotient Bioresearch (Radiochemicals) Ltd. (Cardiff, UK). The binding assays with L-3H-Kyn using mouse liver cytosol from Ahr-proficient and Ahr-deficient mice were performed. Specific binding was defined as the difference of radioactivity between Ahr-proficient and Ahr-deficient cytosol.

Animal Experiments

All animal procedures followed the institutional laboratory animal research guidelines and were approved by the governmental authorities. Human glioma cells were either injected s.c. or stereotactically implanted into the right striatum of six 6-12-week-old athymic mice (CD1nu/nu) and monitored. NK cell depletion was performed by biweekly i.p. injection of rabbit anti-asialo GM1 antibody (Wako Chemicals, Duesseldorf, Germany) starting 2 days before tumor cell injection. Controls were injected with rabbit IgG (Calbiochem, Darmstadt, Germany). For induction of AHR knockdown in vivo doxycycline was administered to the mice at a concentration of 2 mg/ml in ucrosecontaining drinking water. Murine glioma cells were injected s.c. into the right flank of 6-12-week-old wildtype C57BL6/N mice or AHR–/–057/B16 mice.

Magnetic Resonance Imaging (MRI)

MRI scans shown in FIG. 3g were performed using a custom-developed transmit/receive small animal coil in a conventional whole-body 1.5 T MRI scanner (Symphony, Siemens, Erlangen, Germany).

Microarray

U87 glioma cells were treated with 100 µM Kyn for 8 h or 24 h, after which the cells were harvested and RNA isolated using the RNAeasy-Kit (Qiagen). The RNA was subjected to microarray analyses as detailed in the Supplementary Methods. For each of the four treatments (8 h, 24 h, Kyn-treated, untreated) two arrays were hybridised and the mean log 2 ratios of gene expression in Kyn-treated vs. untreated samples were calculated. Further analyses of the data are detailed in the Supplementary Methods. For clinical samples microarray and clinical data were acquired from the REpository for Molecular BRAin Neoplasia DaTa (REMBRANDT) (Supplementary Methods). Survival analysis within the data set of untreated primary glioblastoma (n=362) of The Cancer Genome Atlas (TCGA) network was performed using the Kaplan-Meier-analysis module of the R2 microarray analysis and visualisation platform (http://r2.amc.nl).

Statistical Analysis

Data are expressed as mean±s.e.m. Analysis of significance was performed using the Student's t-test (SigmaPlot). P values<0.05 were considered significant. Correlation of Ki67 and TDO was analysed by Spearman rank correlation (SPSS, IBM, Somers, N.Y., USA). Correlations between TDO and AHR (FIG. 6c) as well as TDO and CYP1B1 (FIG. 6d) were analysed by Spearman rank correlation (Sigma-plot). Nuclear fluorescence intensity was analysed using One-Way ANOVA on ranks (p=<0.001) followed by Dunn's Method (p<0.05).

Example 2

Autocrine and Paracrine Effects of Kyn Generated by TDO

In accordance with the studies underlying the present invention, a screen of human cancer cell lines revealed constitutive degradation of Trp and release of high micromolar amounts of Kyn in brain tumor cells, namely glioma cell lines and gliomainitiating cells (GIC), but not human astrocytes (FIG. 1a). Surprisingly, IDO1 and IDO2 did not account for the constitutive Trp catabolism in brain tumors. Instead, tryptophan-2,3-dioxygenase (TDO), which is predominantly expressed in the liver and believed to regulate systemic Trp concentrations, was strongly expressed in human glioma cells and correlated with Kyn release (FIG. 1b). Pharmacological inhibition or knockdown of TDO blocked Kyn release by glioma cells, while knockdown of IDO1 and IDO2 had no effect (FIG. 1c,d), thus confirming that TDO is the central Trp-degrading enzyme in human glioma cells. In human brain tumor specimens TDO protein levels increased with malignancy and correlated with the proliferation index (FIG. 1e-g). As described previously (Miller 2004, Neurobiol Dis 15(3), 618, healthy human brain showed only weak TDO staining in neurons (FIG. 1e). TDO expression was not confined to gliomas but was also detected in other types of cancers referred to elsewhere herein including hepatocellular carcinoma, colon carcinoma, breast cancer, NSCLC, ovarian carcinoma, malignant melanoma (brain metastatses), and renal cell carcinoma.

Reduced Trp concentrations were measured in the sera of glioma patients (FIG. 1h). These may not have translated into increased Kyn levels (FIG. 1h), because Kyn is taken up by other cells and metabolized to quinolinic acid. Indeed, accumulation of quinolinic acid was detected in TDO-expressing glioblastoma tissue (FIG. 1i). Kyn suppresses allogeneic T cell proliferation9. Allogeneic T cell proliferation inversely correlated with Kyn formation by glioma-derived TDO (FIG. 2a). Knockdown of TDO in glioma cells (Supplementary FIG. 4c,d; Supplementary Note 9) restored allogeneic T cell proliferation, while addition of Kyn to the TDO knockdown cells prevented the restoration of T cell proliferation (FIG. 2b). Kyn concentration-dependently inhibited the proliferation of T cell receptor-stimulated CD4+ and CD8+ T cells (Supplementary FIG. 4e). In addition, knockdown of TDO resulted in enhanced lysis of glioma cells by alloreactive PBMC (Supplementary FIG. 4f). Finally, decreased infiltration with leukocyte common antigen (LCA) positive and CD8+ immune cells was observed in sections of human glioma with high TDO expression in comparison to those with low TDO expression (FIG. 2c), indicating that Kyn formation by TDO may suppress antitumor immune responses. In vivo experiments in immunocompetent mice demonstrated that tumors expressing TDO grew faster and displayed a higher proliferation index than TDO-deficient control tumors (FIG. 2d). TDO activity in tumors suppressed antitumor immune responses in vivo as evidenced by reduced interferon-γ (IFN-γ) release by tumor-specific T cells and tumor cell lysis by spleen cells of mice bearing TDO-expressing tumors in comparison with mice bearing TDO-deficient tumors (FIG. 2e,f).

Next the autocrine effects of Kyn on glioma cells were assessed. While no differences in cell cycle progression were detected between controls and glioma cells with TDO knockdown, knockdown of TDO reduced motility and clonogenic survival (FIG. 2g,h). This was mediated by Kyn as exogenous addition of Kyn restored motility and clonogenic survival in the absence of Trp (FIG. 2i,j), suggesting that Kyn increases the motility of malignant glioma cells. In GIC sphere formation was enhanced in response to Kyn. Finally, tumor formation was impaired when TDO knockdown tumors were orthotopically implanted in the brains of nude mice, which are devoid of functional T cells (FIG. 2k).

Example 3

TDO Mediated Inhibition of N Cells

To analyse whether TDO-mediated inhibition of antitumor NK cell responses, which are functional in nude mice, may account for impaired formation of TDO knockdown tumors, subcutaneous tumor growth was compared in the presence or absence of NK cells. NK cell depletion enhanced the growth of both control and TDO knockout tumors but did not restore the growth of TDO knockout tumors to that of controls (FIG. 2l), suggesting that Kyn generated by constitutive TDO activity enhances the malignant phenotype of human gliomas in an autocrine manner in the absence of functional antitumor T cell and NK cell responses.

Example 4

Molecular Mechanism of Kyn Activity Via AHR

To better understand the molecular mechanisms underlying the autocrine effects of Kyn on glioma cells, microarray analyses of Kyn-treated glioma cells was performed revealing broad induction of AHR response genes by Kyn (FIG. 3a). Pathway analyses showed that the 25 genes that were most strongly induced by Kyn treatment in U87 cells at 8 h and at 24 h were all directly or indirectly regulated by the AHR (FIG. 3a).

Malignant glioma cell lines as well as GIC express the AHR constitutively and upregulation of AHR target genes by Kyn was confirmed in two different glioma cell lines. Kyn led to translocation of the AHR into the nucleus after 1 h, thus showing an immediate effect of Kyn on the AHR (FIG. 3b,c). In accordance, Western blot analyses of Kyn-activated tumor cells showed reduced cytoplasmic localisation paralleled by increased nuclear accumulation of the AHR comparable to that induced by TCDD (FIG. 3d).

Kyn concentration-dependently induced DRE-luciferase activity in glioma cells with an EC50 of 36.6 µM (FIG. 3e). AHR activation was unique to Kyn in a panel of Trp catabolites. An ethoxyresorufin-O-deethylase (EROD) assay confirmed the induction of the functional AHR target gene cytochrome P450, family 1, subfamily A, polypeptide 1 (CYP1A1) with an EC50 of 12.3 µM for Kyn. Radioligand binding assays using mouse liver cytosol from Ahr-proficient and Ahr deficient mice demonstrated that Kyn binds to the AHR with a KD (app) of ≈4 µM (FIG. 3f). Activation of the AHR and upregulation of AHR-regulated gene expression in response to Kyn were inhibited by the AHR antagonist 3,4-DMF or knockdown of the AHR (FIG. 3g), indicating that Kyn is a specific agonist of the AHR. The involvement of the same or similar AHR residues in the binding to Kyn, TCDD and 3-methylcholanthrene (3-MC) was confirmed by the fact that 3,4-DMF inhibited the activation of the AHR by all three ligands. Importantly, the endogenous Kyn production of glioma cells was sufficient to activate the AHR, as knockdown of TDO decreased the expression of AHR regulated genes (FIG. 3h). As mean Kyn concentrations of 37.01+/−13.4 µM were measured in U87 xenografts (n=6), sufficient Kyn concentrations to activate the AHR were also reached in vivo. In accordance with an activation of the AHR by TDO-derived Kyn, expression of the AHR target gene TIPARP in LCA+ immune cells was observed only in human glioma sections expressing TDO (FIG. 4a).

To determine whether TDO influences antitumor immune responses via the AHR the infiltration of immune cells in human glioma sections in relation to their AHR expression was analysed. Indeed, infiltration by LCA+ and CD8+ immune cells was decreased in sections of human gliomas with high AHR expression compared to those with low AHR expression (FIG. 4b). To analyse the contribution of host AHR expression to tumor growth, the growth of murine tumors with and without Tdo expression in Ahr-deficient and Ahr-proficient mice was compared. The growth of Tdo-expressing tumors was attenuated in Ahr-deficient mice when compared with Ahr-proficient mice (FIG. 4c) indicating that AHR mediated host effects enhance tumor growth. Staining of LCA+ immune cells in the tumors revealed that expression of TDO reduced the infiltration with LCA+ immune cells in Ahr proficient mice, but not in Ahr-deficient mice (FIG. 4d), suggesting that TDO-mediated suppression of anti-tumor immune responses via the AHR contributes to the host effects enhancing the growth of Tdo-expressing tumors. In addition, while in Ahr proficient mice Tdo expression strongly enhanced tumor growth in comparison to tumors not expressing Tdo, the same effect was observed in Ahr-deficient mice, albeit to a much lower extent (FIG. 4c). As murine glioma cells express functional AHR, these results suggest that the increase in tumor growth mediated by TDO in Ahr-deficient mice is due to autocrine effects of TDO on the tumor cells themselves. This notion is supported by the fact that Kyn failed to induce motility of human glioma cells after AHR knockdown (FIG. 4e). Also, the increase in clonogenic survival in response to Kyn was abolished in glioma cells with a knockdown of the AHR (FIG. 4f). Finally, in vivo experiments demonstrated that induced knockdown of the AHR in human glioma cells inhibited tumor growth in immunocompromised mice (FIG. 4g), underscoring the importance of AHR signaling for the autocrine effects of Trp degradation.

Next it was investigated whether TDO-derived Kyn activates the AHR in human brain tumor tissue. Indeed, TDO expression correlated with the expression of the AHR and AHR target genes in human glioma tissue (FIG. 5a,b,c), indicating that constitutive TDO expression in glioma cells produced sufficient Kyn levels to activate the AHR. To address whether the TDO-Kyn-AHR signalling pathway is also activated in cancers other than glioma, we analysed microarray data of diverse human tumor entities. Interestingly, TDO expression correlated with the expression of the AHR target gene CYP1B1 not only in glioma (FIG. 5c), but also in B-cell lymphoma, Ewing sarcoma, bladder carcinoma, cervix carcinoma, colorectal carcinoma, lung carcinoma and ovarian carcinoma (FIG. 5d). This finding indicates that the TDO-Kyn-AHR pathway is not confined to brain tumors but appears to be a common trait of cancers. Analysis of the Rembrandt database revealed that the overall survival of glioma patients (WHO grade II-IV) with high expression of TDO, the AHR or the AHR target gene CYP1B1 was reduced compared to patients with intermediate or low expression of these genes (FIG. 5e). Finally, in patients with glioblastoma (WHO grade IV)14, the expression of the AHR targets CYP1B1, IL1B, IL6 and IL8, which are regulated by TDO-derived Kyn in glioma cells (FIG. 3h), were found to predict survival even independent of WHO grade (FIG. 5f), thus further underscoring the importance of AHR activation for the malignant phenotype of gliomas. In summary these data suggest that endogenous tumor-derived Kyn activates the AHR in an autocrine/paracrine fashion to promote tumor progression (FIG. 5g).

The invention claimed is:

1. A method for treating a natural AHR ligand-dependent cancer comprising administering to a subject suffering from the cancer a therapeutically effective amount of an AHR inhibitor, wherein:

(a) the natural AHR ligand is kynurenine, and
   (b) the AHR inhibitor is a flavone or derivative thereof selected from the group consisting of 3,4-dimethoxyflavone, 3'-methoxy-4'-nitroflavone, 4',5,7-Trihydroxyflavone (apigenin), and 1-Methyl-N-[2-methyl-4-[2-(2-methylphenyl)diazenyl]phenyl-IH-pyrazole-5-carboxamide.

2. The method of claim 1, wherein the cancer is selected from the group consisting of brain tumors, glioma, melanoma, colorectal adenocarcinoma, colon carcinoma, renal cell carcinoma, non-small cell lung cancer (NSCLC), breast cancer, hepatocellular carcinoma, ovarian carcinoma, head and neck carcinoma, bladder cancer, pancreatic adenocarcinoma, mesothelioma, and small cell lung cancer (SCLC).

* * * * *

```
                        SEQUENCE LISTING

<160> NUMBER OF SEQ ID NOS: 22

<210> SEQ ID NO 1
<211> LENGTH: 67
<212> TYPE: DNA
<213> ORGANISM: Artificial Sequence
<220> FEATURE:
<223> OTHER INFORMATION: AHR shRNA antisense oligo

<400> SEQUENCE: 1
agcttggatc caaaaaagcg tttaccttca aactttatct cttgaataaa gtttgaaggt    60
aaacgcc                                                             67

<210> SEQ ID NO 2
<211> LENGTH: 67
<212> TYPE: DNA
<213> ORGANISM: Artificial Sequence
<220> FEATURE:
<223> OTHER INFORMATION: AHR shRNA sense oligo

<400> SEQUENCE: 2
tcgaggcgtt taccttcaaa ctttattcaa gagataaagt ttgaaggtaa acgctttttt    60
ggatcca                                                             67

<210> SEQ ID NO 3
<211> LENGTH: 67
<212> TYPE: DNA
<213> ORGANISM: Artificial Sequence
<220> FEATURE:
<223> OTHER INFORMATION: AHR shRNA antisense oligo (Dharmacon siRNA #6
      of Smart pool of AHRAHR siRNA)

<400> SEQUENCE: 3
agcttggatc caaaaaagga actcaagctg tatggtatct cttgaatacc atacagcttg    60
agttccc                                                             67

<210> SEQ ID NO 4
<211> LENGTH: 67
<212> TYPE: DNA
<213> ORGANISM: Artificial Sequence
<220> FEATURE:
<223> OTHER INFORMATION: AHR shRNA sense oligo (Dharmacon)

<400> SEQUENCE: 4 tcagggaac tcaagctgta tggtattcaa gagataccat acagcttgag ttccttttt     60 ggatcca                                                             67

<210> SEQ ID NO 5
<211> LENGTH: 21
<212> TYPE: RNA
<213> ORGANISM: Homo sapiens

<400> SEQUENCE: 5
ucaccaaauc cacgaucauu u                                             21

<210> SEQ ID NO 6
```

-continued

```
<211> LENGTH: 21
<212> TYPE: RNA
<213> ORGANISM: Homo sapiens

<400> SEQUENCE: 6
uuucaguguu cuucgcauau u                                              21

<210> SEQ ID NO 7
<211> LENGTH: 21
<212> TYPE: RNA
<213> ORGANISM: Homo sapiens

<400> SEQUENCE: 7
guaugaaggg uucugggaau u                                              21

<210> SEQ ID NO 8
<211> LENGTH: 21
<212> TYPE: RNA
<213> ORGANISM: Homo sapiens

<400> SEQUENCE: 8
gaacgggaca cuuugcuaau u                                              21

<210> SEQ ID NO 9
<211> LENGTH: 19
<212> TYPE: RNA
<213> ORGANISM: Homo sapiens

<400> SEQUENCE: 9
caaacuuccu caauugauu                                                 19

<210> SEQ ID NO 10
<211> LENGTH: 19
<212> TYPE: RNA
<213> ORGANISM: Homo sapiens

<400> SEQUENCE: 10
uuggaaagcu aucacauau                                                 19

<210> SEQ ID NO 11
<211> LENGTH: 19
<212> TYPE: RNA
<213> ORGANISM: Homo sapiens

<400> SEQUENCE: 11
gaguauggcu uucuucuuc                                                 19

<210> SEQ ID NO 12
<211> LENGTH: 19
<212> TYPE: RNA
<213> ORGANISM: Homo sapiens

<400> SEQUENCE: 12
gcacccaguu gaaguuuaa                                                 19

<210> SEQ ID NO 13
<211> LENGTH: 19
<212> TYPE: RNA
<213> ORGANISM: Homo sapiens

<400> SEQUENCE: 13
ucauaaggau ucaggcuaa                                                 19
```

```
<210> SEQ ID NO 14
<211> LENGTH: 19
<212> TYPE: RNA
<213> ORGANISM: Homo sapiens

<400> SEQUENCE: 14
agugauaggu acaagguau                                              19

<210> SEQ ID NO 15
<211> LENGTH: 19
<212> TYPE: RNA
<213> ORGANISM: Homo sapiens

<400> SEQUENCE: 15
ggauuuaacu ucugggggaa                                             19

<210> SEQ ID NO 16
<211> LENGTH: 19
<212> TYPE: RNA
<213> ORGANISM: Homo sapiens

<400> SEQUENCE: 16
gcgaagaaga caaaucaca                                              19

<210> SEQ ID NO 17
<211> LENGTH: 47
<212> TYPE: DNA
<213> ORGANISM: Artificial Sequence
<220> FEATURE:
<223> OTHER INFORMATION: TDOA shRNA sense

<400> SEQUENCE: 17
ggaaagaact ccaggtttat tcaagagata aacctggagt tctttcc               47

<210> SEQ ID NO 18
<211> LENGTH: 47
<212> TYPE: DNA
<213> ORGANISM: Artificial Sequence
<220> FEATURE:
<223> OTHER INFORMATION: TDOA shRNA antisense

<400> SEQUENCE: 18
cctttcttga ggtccaaata agttctctat ttggacctca agaaagg               47

<210> SEQ ID NO 19
<211> LENGTH: 47
<212> TYPE: DNA
<213> ORGANISM: Artificial Sequence
<220> FEATURE:
<223> OTHER INFORMATION: TDOB shRNA sense

<400> SEQUENCE: 19
tcataaggat tcaggctaat tcaagagatt agcctgaatc cttatga               47

<210> SEQ ID NO 20
<211> LENGTH: 47
<212> TYPE: DNA
<213> ORGANISM: Artificial Sequence
<220> FEATURE:
<223> OTHER INFORMATION: TDOB shRNA antisense

<400> SEQUENCE: 20
agtattccta agtccgatta agttctctaa tcggacttag gaatact               47

<210> SEQ ID NO 21
```

```
<211> LENGTH: 67
<212> TYPE: DNA
<213> ORGANISM: Artificial Sequence
<220> FEATURE:
<223> OTHER INFORMATION: scrambled shRNA antisense oligo

<400> SEQUENCE: 21
agcttggatc caaaaaagta cttccacctc agttggctct cttgaagcca actgaggtgg    60
aagtacc                                                              67

<210> SEQ ID NO 22
<211> LENGTH: 67
<212> TYPE: DNA
<213> ORGANISM: Artificial Sequence
<220> FEATURE:
<223> OTHER INFORMATION: scrambled shRNA sense oligo

<400> SEQUENCE: 22
tcgaggtact tccacctcag ttggcttcaa gagagccaac tgaggtggaa gtactttttt    60
ggatcca                                                              67
```